United States Patent [19]

Ando et al.

[11] Patent Number: 5,149,688

[45] Date of Patent: Sep. 22, 1992

[54] METHODS, COMPOUNDS, AND COMPOSITIONS FOR IMMUNOSUPPRESSION

[75] Inventors: Dale G. Ando, Walnut Creek; Corey H. Levenson, Oakland; Irwin Braude, Vallejo, all of Calif.

[73] Assignee: Cetus Corporation, Emeryville, Calif.

[21] Appl. No.: 513,983

[22] Filed: Apr. 24, 1990

[51] Int. Cl.[5] ............... A61K 31/50; A61K 31/19
[52] U.S. Cl. ............................... 514/254; 514/557
[58] Field of Search ....................... 514/254, 557

[56] References Cited

U.S. PATENT DOCUMENTS 4,670,467  6/1987  Hess et al. ........................ 514/574

OTHER PUBLICATIONS

Chem Abst, 105:202600t (1986). Miller et al.

Primary Examiner—Frederick E. Waddell
Assistant Examiner—Zohreh A. Fay
Attorney, Agent, or Firm—Scott R. Bortner; Gregory J. Giotta; Wean Khing Wong

[57] ABSTRACT

This invention is in the area of immunology, and specifically relates to immunopharmacology as applied to the development of immunosuppressive compositions and methods of use thereof for treating a wide variety of diseases arising from abnormal or undesirable normal immune responses. Compositions and methods of using the same that are particularly useful in treating autoimmune diseases are shown.

2 Claims, 15 Drawing Sheets

METHODS, COMPOUNDS, AND COMPOSITIONS FOR IMMUNOSUPPRESSION

FIELD OF THE INVENTION

This invention is in the area of immunology, and specifically relates to immunopharmacology as applied to the development of immunosuppressive compositions and methods of use thereof for treating a wide variety of diseases arising from abnormal or undesirable normal immune responses. Compositions and methods of using the same that are particularly useful in treating autoimmune diseases are shown.

BACKGROUND OF THE INVENTION

This invention relates to methods and compositions for immunosuppression. The following presents the general background of diseases that arise from abnormal or undesirable normal immune responses. Rheumatoid arthritis is discussed as an example of these diseases. Further, a background discussion of succinylacetone, methotrexate, and derivatives of methotrexate as examples of the immunosuppressive compositions, is presented.

DISEASES OF THE IMMUNE SYSTEM

There is a continuous search for therapeutics that have immunosuppressive activity, for treating diseases arising from abnormal or undesirable normal immune responses. Examples of undesirable normal immune responses are immune-rejections arising from transplantations of cells, tissues, or organs; and examples of abnormal immune responses are autoimmune diseases. Autoimmunity can generally be defined (Smith, H. and Steinberg, A. Autoimmunity—A Perspective *Ann. Rev. Immunol.* 1:175 (1983)) as the generation of an immune response against a person's own self components. Autoimmune diseases generally develop spontaneously in humans. Both a person's genetic predisposition, as well as environmental factors may play a role. Those agents which are thought to initiate autoimmunity are poorly defined. However, autoimmunity can be induced in experimental animals by suitable immunization procedures with known antigens. Classical examples of experimentally induced autoimmune diseases in animals are experimental or allergic encephalomyelitis, and adjuvant induced arthritis. The former is induced by immunization with a myelin basic protein, and induces an autoimmune disease having neurological symptoms involving partial or complete paralysis of the animals. The latter entails use of *Mycobacterium Tuberculosis* (hereinafter referred to as M.Tb) for induction of arthritis in rats. The adjuvant arthritis (AA) model has been extensively used for evaluation of both antiinflammatory and immunosuppressive therapies. The adjuvant arthritis model in susceptible strains of rats is a prototypic model of chronic T lymphocyte dependent arthritis induced by immunization with M.Tb. The pathogenetic mechanism of arthritis is mediated by T helper cells and adoptive transfer of M.Tb reactive, T cell enriched lymph nodes or T cell clones results in signs of arthritis. The histologic appearance of the arthritic joint is similar to that of rheumatoid arthritis except for an increase in periostitis and new bone formation. A destructive, deforming joint lesion is clearly induced and the disease follows a monophasic, non-relapsing course.

Examples of autoimmune diseases in humans include: various forms of diabetes (e.g., diabetes mellitus), systemic lupus erythematosus, myasthenia gravis, autoimmune encephalitis, chronic thyroiditis, hemolytic anemia, multiple sclerosis, vasculitis, and rheumatoid arthritis.

Immunosuppressive drugs are used to treat autoimmune diseases, much as they are used to treat organ tissue transplants and graft versus host disease. In the clinical arena, cyclosporin A has been shown to be effective in treating various experimentally induced autoimmune diseases. Shevach, E. *Ann. Rev. Immunol.* 3:397 (1985). These include experimental allergic encephalomyelitis, and an autoimmune form of diabetes which develops in non-obese diabetic (NOD) mice. Similarly, cyclosporin A has been applied in the clinical setting, and used to treat patients with posterior uveitis. It has also been used to treat type-1 diabetes mellitus in humans. Despite these results, however, cyclosporin A has side effects which has limited its use in the clinic. In addition to cyclosporin A, other immunosuppressive drugs have been shown to have a degree of efficacy when used to treat various autoimmune disease.

RHEUMATOID ARTHRITIS

Rheumatoid arthritis (hereinafter referred to as RA) is a chronic progressive inflammatory arthritis involving multiple joints, characterized by a tendency to spontaneous remissions and subsequent relapses. Kissane, J. M. (ed.), 1985, *Anderson's Pathology*, II:1828. As used in this patent application, RA is defined to also include juvenile rheumatoid arthritis (JRA). RA has many manifestations which affect different parts of the body. As a simple definition, RA is a disease of articular joints in which the cartilage and bone is slowly eroded away by a proliferative, invasive connective tissue, called pannus, which is derived from the synovial membrane and it may involve peri-articular structures such as bursae, tendon sheaths, and tendons as well as extra-articular tissues such as the subcutis, cardiovascular system, lungs, spleen, lymph nodes, skeletal muscles, central and peripheral nervous system and the eyes. Id.. The following symptoms are indications of a poor prognosis: subcutaneous nodules, vasculitis, neuritis, pleuropulmonary disease, pericarditis, Sjogren's syndrome, and Felty's syndrome. Ancillary abnormalities of RA include: anemia, elevated erythrocyte sedimentation rate, high titer serum rheumatoid factor, and inflammatory synovial fluid. The affected bone is demineralized, eroded, then deformed. Katz, W. A., 1985, *Am. J. Med.*, 79:24, entitled "Modern Management of Rheumatoid Arthritis". The origin of RA is as yet not fully comprehended.

Recent studies suggest the involvement of both humoral and cell-mediated immune responses (CMI) in the underlying chronic inflammatory reaction occurring in the joint. Rheumatoid factor is RA's most widely recognized serum marker. In one scenario, a virus, small bacterium, or some other agent induces an inflammatory defense response that persists in some patients. By-products of the immune reaction inflame the synovium (i.e., prostaglandins, oxygen radicals) and triggers destructive joint changes, (i.e., collagenase), which cause pain, stiffness, functional impairment, and fatigue in patients. Id.

To data, the different treatments of RA have proved unsatisfactory. Traditionally, non-steroidal anti-inflammatory drugs (NSAIDS), such as aspirin and aspirin-like drugs, are used for symptomatic treatment of RA in humans. Steroids have also been used. However, though steroids provide symptomatic relief, they do not prevent destruction caused by arthritis. Steroids can also lead to diabetes, cataracts, and increased rate of infections. Additionally, there is often a rapid reappearance of the active disease when treatment is ended. On the other hand, clinicians over the years have used a number of drugs which they argue reduce the erosive progression of RA. These drugs are termed fundamental or disease modifying drugs, or disease modifying anti-rheumatic drugs, DMARDs. These DMARDs include for example: gold salts; metal chelators such as D-penicillamine; anti-malarial drugs such as chloroquine, dapsone, and sulfasalazine.

Cytotoxic and immunosuppressive drugs have also been used to control RA. Methotrexate and cyclophosphamide are both immunosuppressive and cytotoxic. The immunosuppressive drugs include cyclosporin and corticosteroids.

SUCCINYLACETONE

Succinylacetone (hereinafter referred to as SA) is a seven carbon organic ketoacid. It is a new immunosuppressive compound that was first noted in the urine of patients with hereditary tyrosinemia due to a deficiency of fumarylacetoacetate hydrolase. SA is a potent inhibitor of delta-aminolevulinic dehydratase, the second enzyme of the heme biosynthetic pathway. The immunosuppressive effects of SA were discovered in its ability to enhance tumorigenicity of allogeneic tumors in rats. SA has been used alone to control lethal graft-versus-host disease (Hess, U.S. Pat. No. 4,670,467, issued Jun. 2, 1987); and experimental uveitis in rats. Skolik, S. A., et al., 1988, *Clin. Immunol. Immunopathol.*, 49(1):63-71.

METHOTREXATE

Methotrexate (hereinafter referred to as MTX) is an anti-metabolite and immunosuppressive drug. MTX is also cytotoxic. It is an anti-folate, as a folic acid analogue in inhibits dihydrofolate reductase. MTX is used in combination with cyclosporin A in Graft-versus-host disease (GVHD) prophylaxis. MTX is used alone in the treatment of RA, psoriasis, and autoimmune polymyositis. During the last decade, it has gained acceptance among rheumatologists as an effective treatment for patients with RA that are unresponsive to conventional DMARDs. MTX's onset of action is short (2-3 months) compared to other DMARDs in use. A study involving RA patients receiving the DMARDs gold salts, D-penicillamine, and sulfasalazine, demonstrated that the overall probability of continuing to take any of these three drugs was less than 20% at 5 years (19% for sulfasalazine, 17% for D-penicillamine, and 8% for gold salts). Situnayake R. D. et al., *Ann Rheum Dis*, 46: 177-183 (1987), "Long term treatment of rheumatoid arthritis with sulphasalazine, gold, or penicillamine: a comparison using life-table methods". It was also noted that the cumulative probability of still taking any of these three drugs decreased steadily, but toxic effects were more important early, and lack of efficacy became more important later, in the five-year course of study. In comparison, the probability of continuing MTX therapy for up to 6 years is nearly 50%. Alarcon, G. S., et al., 1989, *Arthritis & Rheumatism*, 32:671, "Methotrexate in Rheumatoid Arthritis". (Hereinafter referred to as the "Alarcon Study".) However, the probability of developing a major or minor toxic event in the case of MTX is significant. Id. The Alarcon Study demonstrated that toxicity, and not efficacy, is the main limiting factor in maintaining a patient on MTX therapy, a clear difference from other DMARDs. Among the potential toxic side effects of MTX are myelosuppression, pneumonitis, GI, thrombocytopenia, and hepatic toxicity. MTX's efficiency in GVHD is similarly limited by its toxicity. Clearly, there is a need for minimizing MTX's toxic effect, but yet maintaining its efficacy.

The effect of low dose MTX on rat adjuvant arthritis model had been reported in Welles, W. L., 1985, *J. Rheum.*, 12:904-906, entitled "Studies on the Effect of Low Dose Methotrexate on Rat Adjuvant Arthritis".

SUMMARY OF THE INVENTION

One aspect of the invention is a method for treating diseases arising from abnormal or undesirable normal immune responses, by means of immunosuppressive compositions. Preferably the diseases are autoimmune diseases, including but not limited to, rheumatoid arthritis (RA), multiple sclerosis, autoimmune encephalitis, chronic thyroiditis, hemolytic anemia, systemic lupus erythematosus, diabetes mellitus, vasculitis, and myasthenia gravis. Also preferred are normal immune responses, for example, immune-rejections arising from transplantations of cells, tissues, or organs.

One aspect of the invention presents a combined SA and MTX treatment of RA. In the AA model, the combined SA and MTX treatment has the advantage of achieving the same result with a lower dosage of SA and MTX compared to each of the compounds alone. Further, the invention presents a surprising result in that the therapeutic benefit of the combined SA and MTX treatment lasted even after treatment has ceased. The above effects allow less frequent administration and lower dosage of SA and MTX, thereby reducing any toxic effect.

Another aspect of the invention presents methods of treating diseases arising from abnormal or undesirable normal immune responses in an afflicted animal, wherein the animal is treated with one or more member(s) selected from the class of acetoacetyl carboxylic acids (the class of acetoacetyl carboxylic acids is hereinafter referred to as ACA. Further, it is hereinafter understood that in a composition or treatment utilizing ACA, one or more member(s) of the ACA class is/are to be utilized), or a combination of two or more of the following: SA, FA, and ACA. "FA" is hereby defined to mean the class of compounds including MTX, derivatives of MTX, and folic acid analogues having immunosuppressive activities. It is hereinafter understood that in a composition or treatment utilizing FA, one or more member(s) of the class of FA is/are to be utilized. The animal can further be treated with other disease modifying antirheumatic drugs (DMARDs), cytotoxic drugs, immunosuppressive drugs, and/or steroids.

A further aspect of the invention presents compositions for treating diseases arising from abnormal or undesirable normal immune responses, wherein the compositions consist of ACA, or a combination of two or more of the following: SA, FA, and ACA. The preferred member of FA and ACA is MTX and 2-acetoacetyl benzoic acid (hereinafter referred to as ABA) respectively. The compositions can further consist of DMARDs, cytotoxic drugs, immunosuppressive drugs, and/or steroids.

A further aspect of the invention presents ACA and examples of its members and compositions, which can be used for treating diseases arising from abnormal or undesirable normal immune responses. ACA has the general formula of:

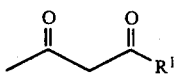

R' is a cyclic saturated or unsaturated group to which is attached a carboxylic acid. In the case of cyclic groups, the ring may contain 3-7 atoms of which one or more may be heteroatoms (such as N, O, S, or P). The extent of unsaturation of the ring may vary. In addition to the carboxylate, other substituents may be present on the ring to enhance aqueous solubility or other pharmacodynamic properties. The unsaturated group may be either a double bond (oriented cis or trans) or a triple bond.

A further aspect of the invention presents ABA, a member of ACA, which can be used for treating diseases arising from abnormal or undesirable normal immune responses. ABA has the general formula of:

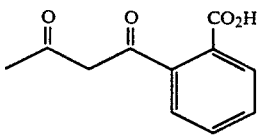

DETAILED DESCRIPTION OF THE INVENTION

Figure 1:
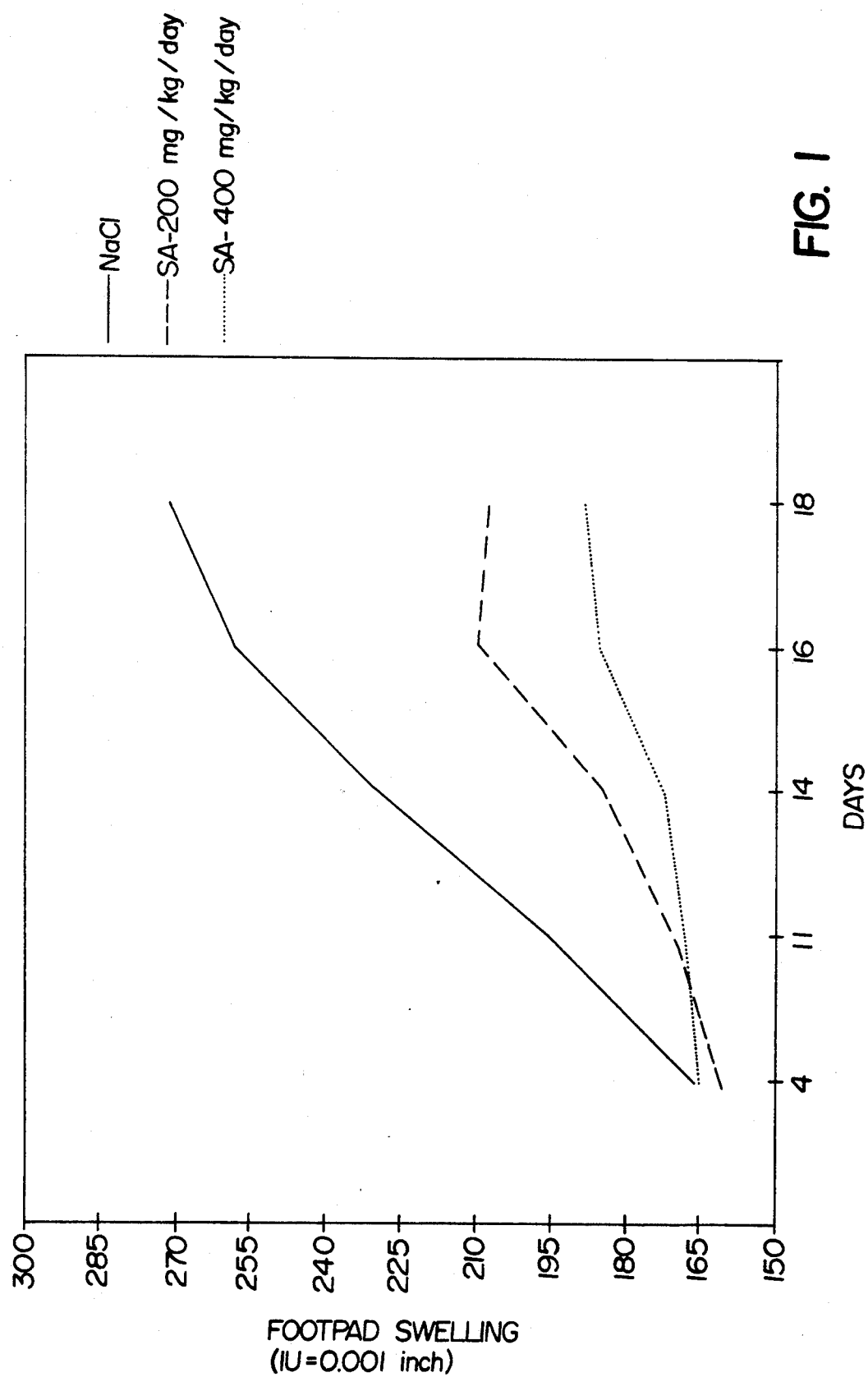
FIG. 1 presents the right footpad swelling measurements in rats in the prophylactic SA treatment regimen.

The invention described herein draws on published work and pending patent applications. By way of example, published work consists of scientific papers and patents. All of these publications and applications, cited previously or below are hereby incorporated by reference.

The invention described herein presents methods and compositions for treating diseases arising from abnormal or undesirable normal immune responses. Preferably, the diseases are autoimmune diseases, including but not limited to, rheumatoid arthritis (RA), multiple sclerosis, autoimmune encephalitis, chronic thyroiditis, hemolytic anemia, systemic lupus erythematosus, diabetes mellitus, vasculitis, and myasthenia gravis. Also preferred are diseases arising from normal immune responses, for example, immune-rejections arising from transplantations of cells, tissues, or organs.

The invention presents methods of treating diseases arising from abnormal or undesirable normal immune responses in an afflicted animal, wherein the animal is treated with one or more member(s) selected from the class of acetoacetyl carboxylic acids (the class of acetoacetyl carboxylic acids are hereinafter referred to as ACA. Further, it is hereinafter understood that in a composition or treatment utilizing ACA, one or more member(s) of the ACA class is/are to be utilized), or a combination of two or more of the following: SA, FA, and ACA. "FA" is hereby defined to mean the class of compounds including MTX, derivatives of MTX, and folic acid analogues having immunosuppressive activities. It is hereinafter understood that in a composition or treatment utilizing FA, one or more member(s) of the class of FA is/are to be utilized.

The methods of the invention include administering to an animal afflicted with a disease arising from an abnormal or undesirable normal immune response, an effective amount of ACA, or a combination of two or more of the following: SA, FA, and ACA. The animal can further be treated with other disease modifying antirheumatic drugs (DMARDs), cytotoxic drugs, immunosuppressive drugs, and/or steroids. These treatments are to either prevent, ameliorate, and/or retard the disease, or its progression in the afflicted animal. The SA and FA; SA and ACA; ACA and FA; ACA, FA and SA treatments are hereinafter respectively referred to as: combined SA and FA; combined SA and ACA; combined ACA and FA; combined ACA, FA and SA treatments. The preferred member of FA and ACA is MTX and ABA respectively. Treatment using SA and the preferred MTX is hereinafter referred to as combined SA and MTX treatment. It is within the scope of this invention that all these treatments can be used to treat the diseases arising from abnormal or undesirable normal immune responses mentioned above. The preferred member of the class of ACA is 2-acetoacetyl benzoic acid (ABA). Preferably, the diseases are autoimmune diseases. The preferred autoimmune disease is RA.

As shown in the experiments below, the preferred combined SA and MTX treatment has the advantage of achieving the same result with a lower dosage of SA and MTX as compared to each of the compounds alone. In the combined SA and MTX treatment, a lower dosage of MTX reduces the toxicity of the drug while maintaining its efficacy. Similarly, the SA dosage required to achieve the same, or better result, is much lower. Thus, any toxicity in SA usage is lowered. Furthermore, this invention presents a surprising result in that the therapeutic benefit of the combined SA and MTX treatment persists even after the treatment has terminated. Thus, less frequent administrations of SA and MTX are required. This is in stark contrast with treatments involving SA alone, shown in the following experiments, which are most effective if administered in a continuous infusion regimen, in order to maintain its therapeutic effect in adjuvant arthritis.

A further aspect of the invention presents the class of ACA and examples of its members which can be used for treating diseases arising from abnormal or undesirable normal immune responses.

The general formula for the class of ACA is as follows:

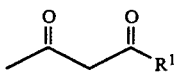

R' is a cyclic saturated or unsaturated group to which is attached a carboxylic acid. In the case of cyclic groups, the ring may contain 3-7 atoms of which one or more may be heteroatoms (such as N, O, S, or P). The extent of unsaturation of the ring may vary. In addition to the carboxylate, other substituents may be present on the ring to enhance aqueous solubility or other pharmacodynamic properties. The unsaturated group may be either a double bond (oriented cis or trans) or a triple bond.

Such compounds may preferably be synthesized by either of two routes; by acetylation of corresponding methyl ketone (Path A), or by reaction between the magnesium complex of t-butyl acetoacetate and an appropriately protected acyl chloride (Path B).

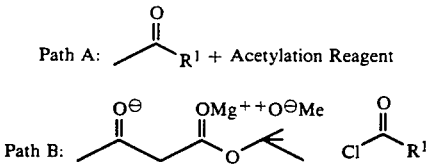

Other methods for synthesizing the desired diketones can be arrived at by modifying the pathways reviewed in Hauser, C. R., et al., "The Acylation of Ketones to Form β-Diketones or β-Keto Aldehydes", in Roger, A., (ed.), 1954, *Organic Reaction*, (John Wiley & Sons, N.Y.) 8: 59-196, Chpt. 3, and the modifications can be arrived at by those with ordinary skill in the art.

Although any similar or equivalent methods and material may be employed in the practice or testing of the present invention, the preferred methods and materials are now described.

The following studies used rats to simulate rheumatoid arthritis, the rat model for RA is AA. In this rat model, the clinical expression of AA generally begins 10 days after immunization with M.Tb. The first set of experiments (Examples 1-2) indicated that SA is active in reducing the incidence and severity of rheumatoid arthritis in a prophylactic and therapeutic manner. A 100% incidence of arthritis indicates a clinical score of equal to or above 1. (For definition of clinical score, see Table 1.) The second set of experiments (Examples 3 and 4) compared the efficacy of SA and MTX treatments. The third set of experiments (Example 5-6) showed the effectiveness and advantages of a combined SA and MTX treatment. The fourth set of experiments (Example 7) presents ACA, a class of compounds that are useful in treating diseases arising from abnormal or undesirable normal immune responses. Methods for making ACA are also presented. The ACA member exemplified is ABA, preferably for the treatment of RA. Example 8 presents methods for treating diseases arising from abnormal or undesirable normal immune responses, using the example of RA in humans.

Having generally described what the applicants believe their invention to be, the following examples are presented to illustrate the invention, and are not to be construed as limiting the scope of the invention.

It would be appreciated by those skilled in the art that the doses presented below are the preferred doses. It should be noted that the effective doses, for example of MTX, may vary from the preferred range shown below depending on the different formulations, routes, dose schedules, increased arthritogeneicity in the M.Tb strains used to induce the disease, and/or other variables known to those skilled in the art. However, those skilled in the art would be able to arrive at other effective doses using techniques known in the art.

Thus, for example, it is within the scope of the invention that the doses of the different compounds, or the member of ACA or FA selected for treating a particular disease arising from an abnormal or undesirable normal immune response can be varied to achieve a desired therapeutic effect.

With the above in mind, it should be noted that Examples 1-6 are representative examples chosen from a set of experiments, run in triplicate, involving different doses of SA and/or MTX. In the therapeutic treatment of AA using SA alone, it was found that SA suppressed AA without causing death or weight loss in the rats, at a SA level of 300 to 400 mg/kg/day continuous infusion (CI), or alternatively, at a daily intraperitoneal (IP) injection of 800 mg/kg/day. The CI regimen was more effective than the IP regimen at suppressing the AA.

In the therapeutic treatment of AA using MTX alone, 2.4 to 4.8 mg/kg/week of MTX was administered as IP injections three times a week. At these doses, MTX suppressed AA. However, the 4.8 mg/kg/week regimen showed toxicity in that some of the rats died or suffered from bleeding noses.

In the SA and MTX combined treatment regimen, the SA was administered in an amount ranging from 150-300 mg/kg/day. The MTX was administered three times a week in IP injections, at a total of 0.9 mg/kg/week. These treatments effectively suppressed AA.

EXAMPLE 1

Prophylactic Effect of SA on Adjuvant Arthritis in Rats

The following experiments (Example 1-2) show that SA treatment, when given in a prophylactic and therapeutic regimen, prevented the development of arthritis.

A. Experimental Methods

1. Animals

Male Lewis rats, 200-250 gm, were obtained from Charles River Laboratory and were housed in the animal care facility. Animals were allowed chow and water ad libitum.

B. Induction of Arthritis

1. Materials

Various lots and sources of mineral oil and Mycobacterium Tuberculosis (H37RA, Difco Laboratories, Detroit, Mich., U.S.A.) were pre-screened for maximal activity in inducing adjuvant arthritis. Maximal activity is defined as the ability to induce 100% disease incidence by day 14 in 10 animals.

2. Immunization

Each of the animals was injected, on day 0, in the footpad of its left hindpaw with 100 µl of an emulsion of M.Tb in mineral oil (10 mg/ml).

3. Measurement of Arthritis Severity

During day 0–7 an acute swelling occured in the injected footpad. This inflammation was a direct result of the adjuvant properties of M.Tb and was caused by macrophages and neutrophils. After about day 12, arthritis developed in the right hind foot and the upper extremities. This arthritis was due to inflammation induced by lymphocytes reactive with M.Tb. This arthritis reached maximal clinical severity by about day 20 and progressive swelling continued past day 30. The severity of the arthritis was assessed using two methods. The first consisted of measuring the diameter of the footpad of each rat's right hindpaw, using a constant tension caliper. The second, a more general indicator of the overall arthritis status of the animal, consisted of numerical scoring for arthritis severity as shown in Table 1.

TABLE 1

Clinical scoring system:

a) Right Footpad
0-no erythema or swelling
1-mild swelling or erythema, <25% of joints
2-arthritis in <50% of joints
3-arthritis in >50% of joints
4-arthritis in all joints
b) Upper extremities:
1-unilateral arthritis
2-bilateral arthritis The maximum score per animal is 6. A clinical score greater than 2 is indicative of a chronic deformity. The observer was blinded to the treatment protocol.

4. Formulation and Administration of SA

SA is an acidic, water soluble powder. It was neutralized to pH 7 with 5–10N NaOH. Since the different lots of SA used had differing buffering capacities for base, the molarity of the neutral sodium SA salt varied from 2.5 to 3.5M. NaCl, isotonic and isovolumic with the highest molar concentration of SA in a particular experiment, was used as a saline treatment for the control in each experiment.

5. Administration of SA

SA was administered by subcutaneous ALZET pumps. These pumps secreted 2 ml of fluid over the course of 14–15 days. The pumps were surgically placed subcutaneously in the dorsal, mid-scapular regions of the rats. In some experiments SA was administered by daily intraperitoneal injection of neutralized SA and isotonic saline.

6. Experiment 1

In these studies SA was administered at doses of 400 and 200 mg/kg/day by ALZET pumps. Isotonic and isovolumic saline was used as the control in this subcutaneous infusion treatment regimen (hereinafter referred to as SQ, or continuous infusion, CI, regimen). The treatment was started on day -4 prior to M.Tb injection (day 0). The pumps were calculated to infuse until day 10. Ten rats were used in each group.

C. Results and Discussion

Figure 2:
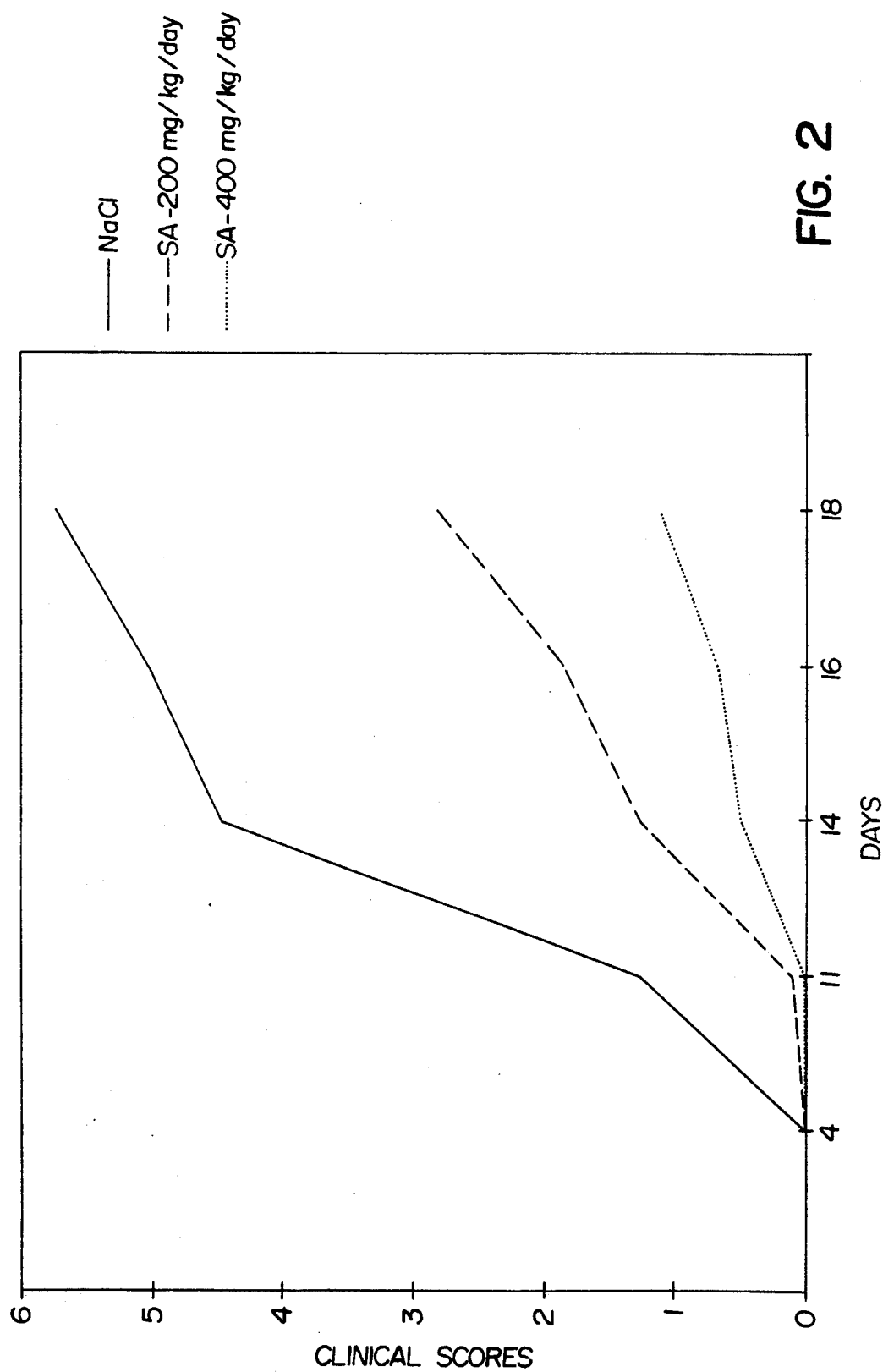
FIG. 2 presents the clinical scoring over time for the SA prophylactic treatment regimen in rats.

Measurement of the right footpad swelling and arthritis in non-injected extremities showed suppression of clinical arthritis and that SA inhibited arthritis severity in a dose dependent manner (see FIG. 1, right footpad measurement and FIG. 2, clinical scores). A cohort of SA treated animals were sacrificed and histology of the joints were investigated. SA was found to suppress histologic arthritis.

Three rats in the group receiving 400 mg/kg/day of SA were sacrificed on day 9. Their plasma SA levels were obtained and assayed by HPLC (High Pressure Liquid Chromatography). The SA levels associated with clinical suppression of arthritis were in the 40–50 µM range (see Table 2).

TABLE 2

Plasma Levels of SA During CI Therapy (400 mg/kg/day)
Blood was Collected on Day 9

| Rat Number | SA Level (µM) |
| --- | --- |
| SA-C1 | 44 |
| SA-C2 | 50 |
| SA-C3 | 50 |
| NaCl | <10 |

Figure 3:
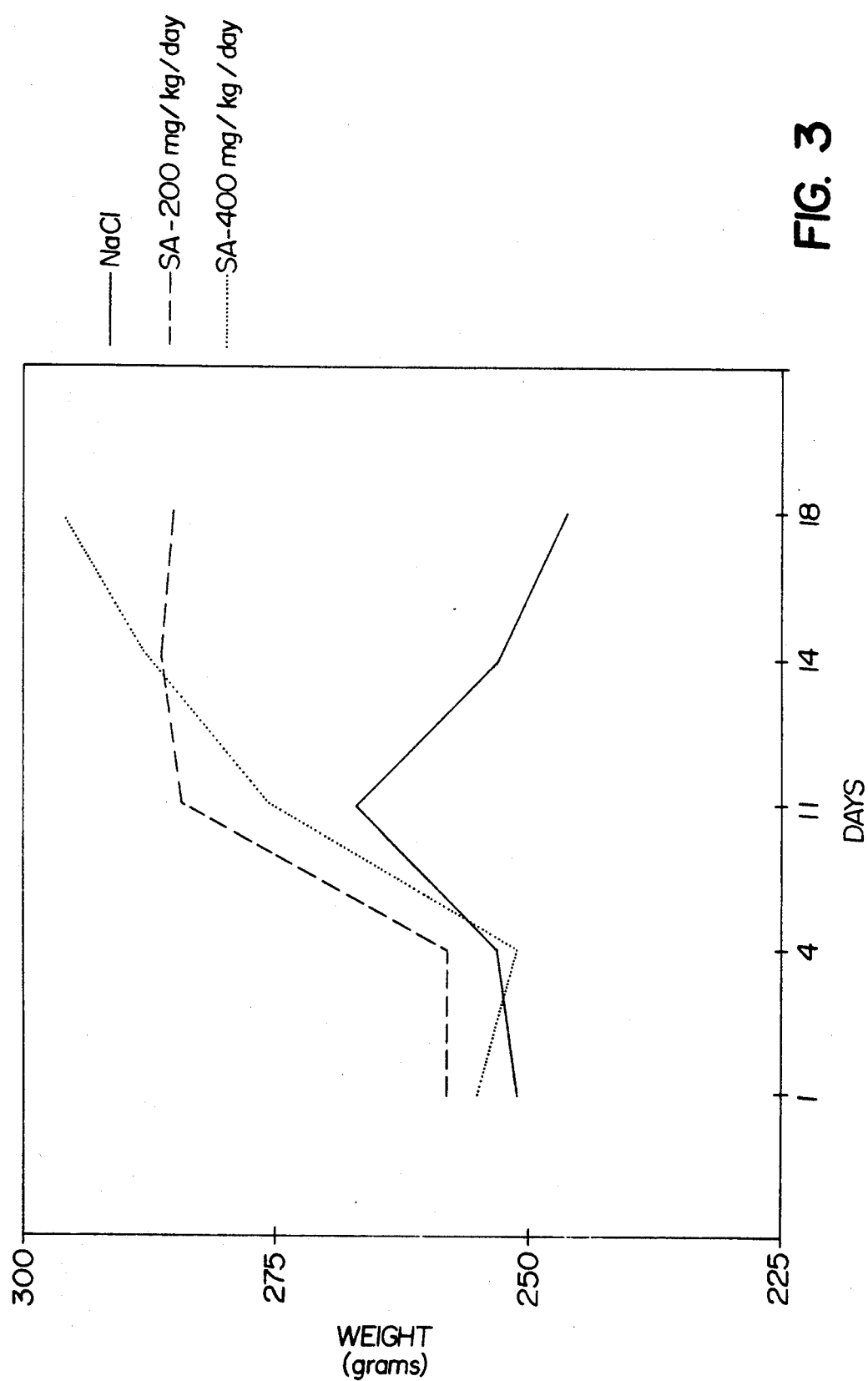
FIG. 3 presents the body weight of the rats in the prophylactic SA treatment regimen.

Animals which develop arthritis usually also lose weight. Even though toxic medications can suppress adjuvant arthritis, these medications usually cause further weight loss. The SA treatment presented here suppressed AA and yet allowed weight gain (see FIG. 3). This suggests that SA is non-toxic to the animals at the level necessary for suppression of AA.

EXAMPLE 2

Therapeutic Effect of SA on AA

The following experiments examined the therapeutic effect of SA on the progression of AA. In these studies, the treatments with SA began at day 5 after the rats had been immunized with M.Tb in their left footpads. At this time, the activation of lymphoid cells with M.Tb was well established and the appearance of mononuclear cells at the joint has been reported as the earliest histologic findings. Billingham, 1983, *Pharma. Theory*, 21: 389.

Figure 4:
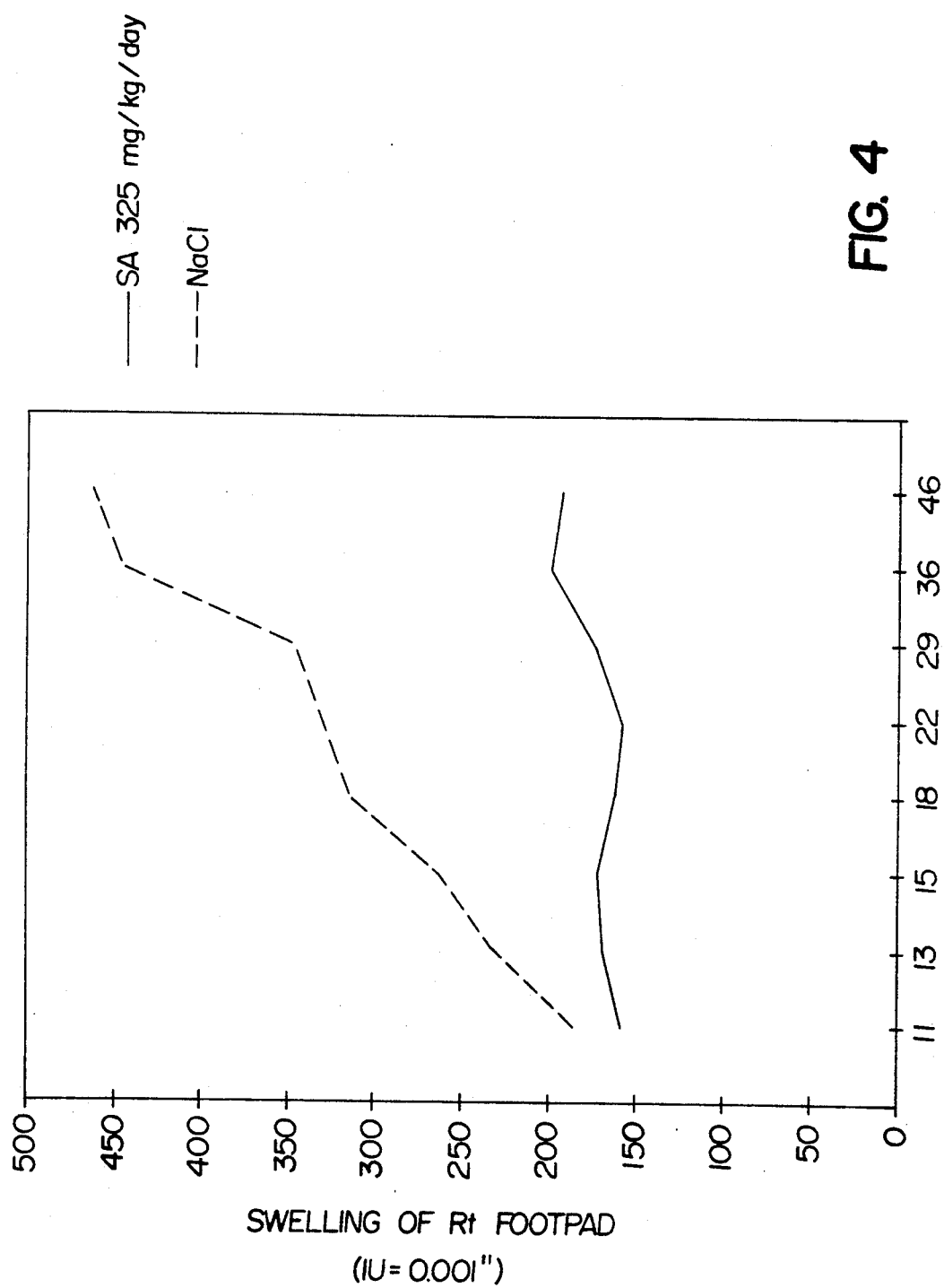
FIG. 4 presents the right hindpaw swelling of the rats in the therapeutic treatment of adjuvant arthritis (AA), in which the SA was continuously and subcutaneously (hereinafter referred to as SQ) infused into the rats.
Figure 5:
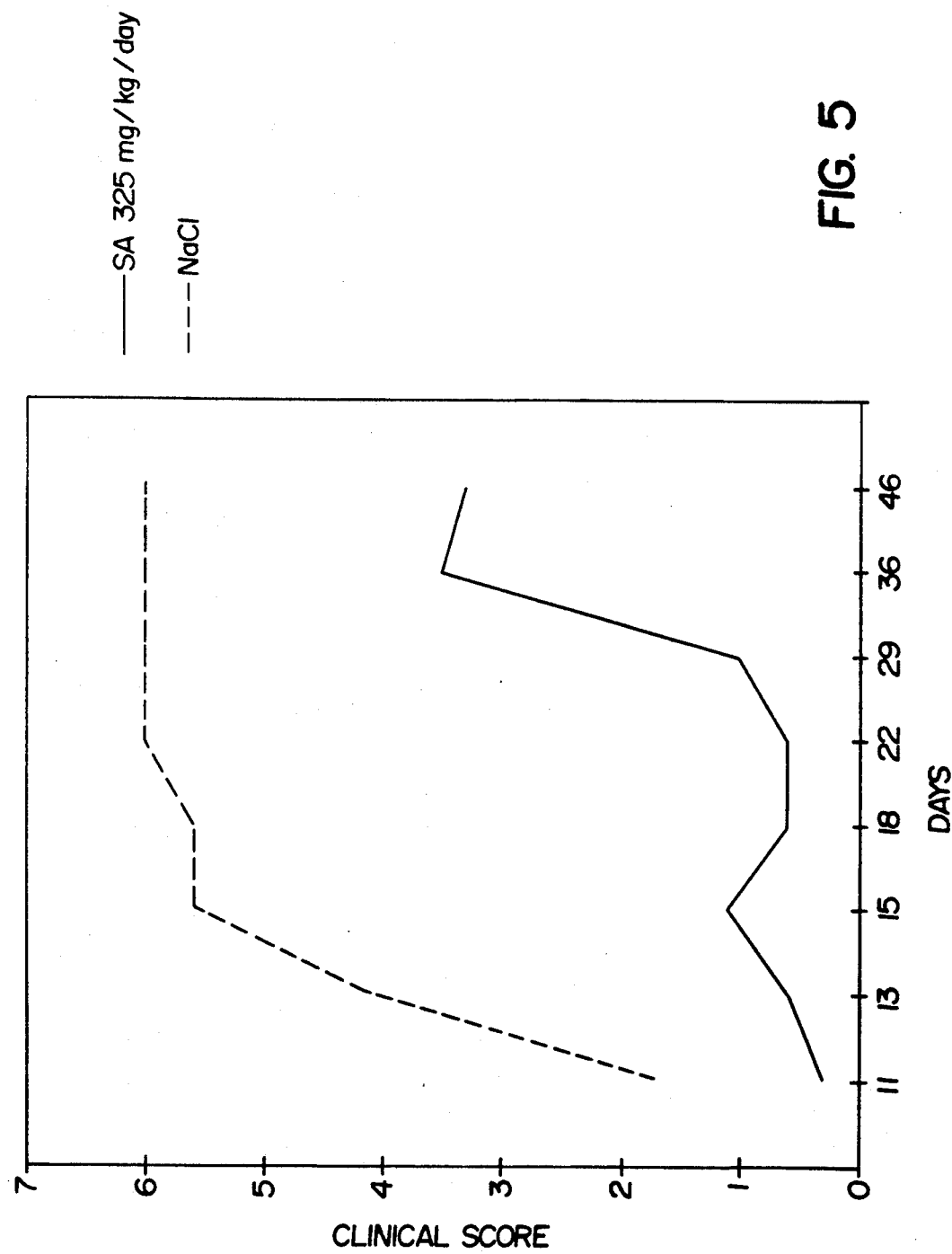
FIG. 5 presents the clinical severity of arthritis in rats in the therapeutic treatment of AA, in which the SA was continuously and subcutaneously infused into the rats.

325 mg/kg/day of SA was administered by subcutaneous pump infusion from day 5 until day 19. The control animals received isotonic and isovolumic NaCl control. Right hindpaw swelling and clinical severity of arthritis was suppressed by SA treatment (FIGS. 4 and 5).

Figure 6:
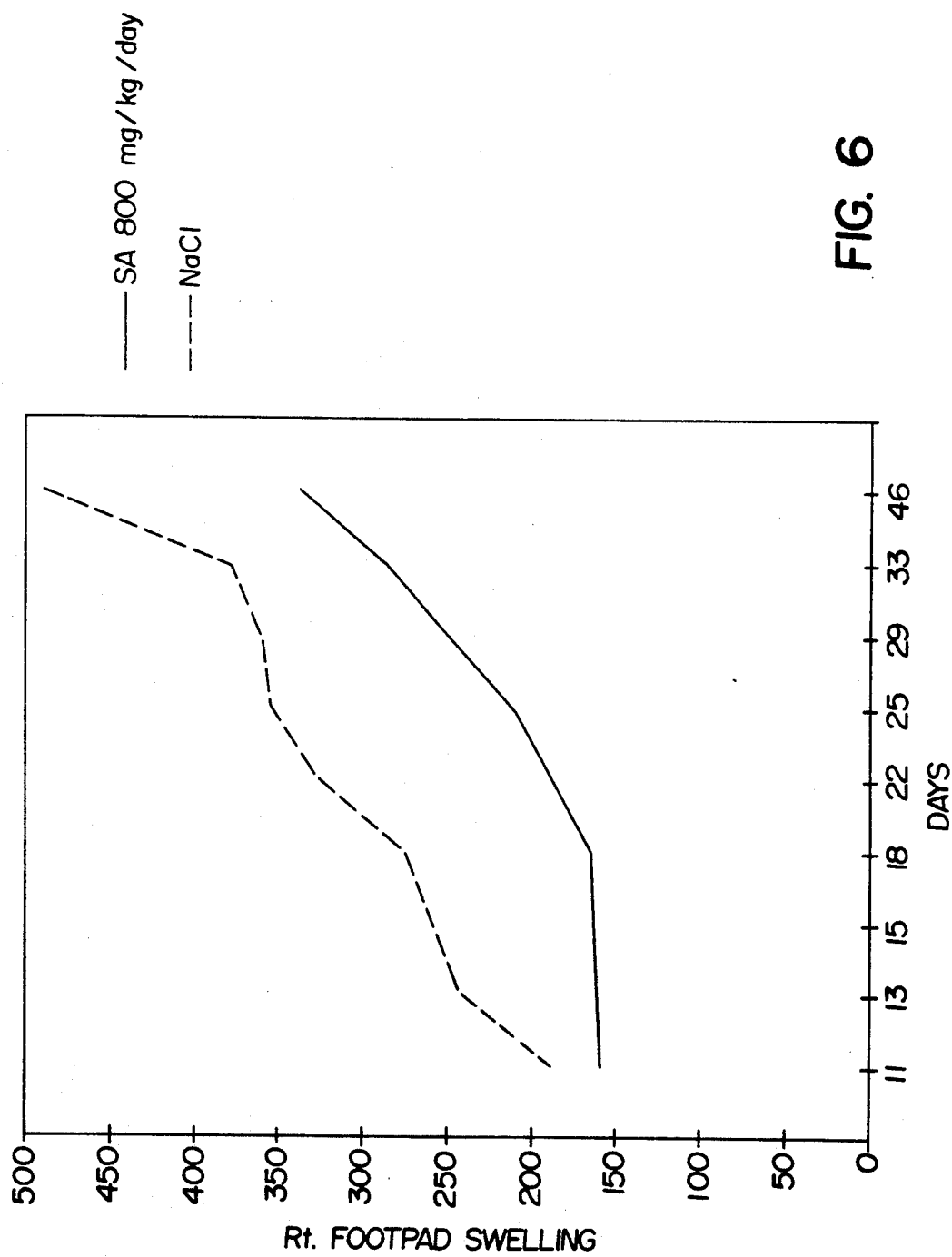
FIG. 6 presents the right hindpaw swelling of the rats in the therapeutic treatment of AA, in which the SA was given as a single daily intraperitoneal (hereinafter referred to as IP) injection into the rats.
Figure 7:
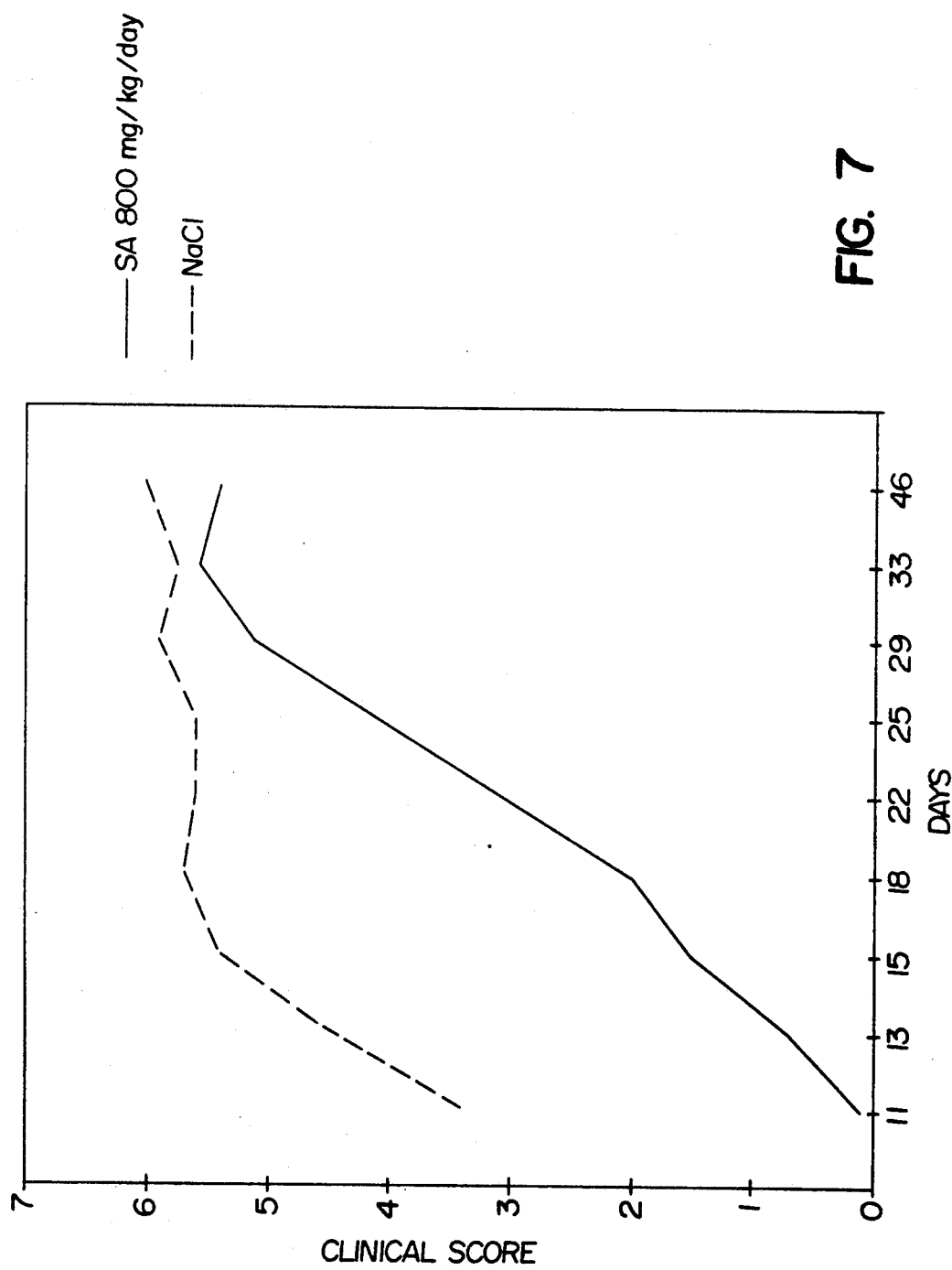
FIG. 7 presents the clinical severity of arthritis in rats in the therapeutic treatment of AA, in which the SA was given as a single daily intraperitoneal injection into the rats.

A parallel group of animals were treated with daily intraperitoneal injections of 800 mg/kg/day of SA (FIGS. 6 and 7). This was done to compare the relative efficacy of continuous infusion versus a single daily intraperitoneal injection.

A. Results

Both the continuous infusion and daily IP injections treatment regimens resulted in suppression of arthritis. The results with continuous infusion were superior in that 1) the arthritis was completely suppressed during treatment, and 2) the clinical scores did not increase until day 36 and this increase was less than half of the saline treated animals. Daily IP injections resulted in the suppression of footpad swelling until the treatment stopped. After the termination of the treatment, an attenuated increase in footpad swelling was observed, however, the swelling was less than that found in the controls. The daily IP injections also delayed the clinical severity of the arthritis, with groups reaching equivalent severity to the controls by day 33. These data show that 1) SA, administered by CI and IP routes, is effective in suppressing arthritis when given after activation of the immune system, and 2) continuous infusion results in greater suppression at a lower dose than does daily IP injection.

EXAMPLE 3

Comparative Efficacy of MTX and SA in Suppressing Onset of AA

Since MTX is an effective treatment of RA in clinical practice, Examples 3 and 4 compare the efficacy of SA and MTX in suppressing AA.

A. Methods

Methotrexate (Sigma, St. Louis, Mo.) was dissolved in 0.9% NaCl. Stock concentrates of MTX were made weekly and were diluted to 200 $\mu$l per dose on the day prior to injection. No further attempts to formulate or assess stability with these methods were made.

Five days after the Lewis rats had been immunized with M.Tb, as in Example 1, the rats were separated into four groups, each group with 10 animals. On the same day, pumps were surgically implanted into the first two groups. The first group received SA at 300 mg/kg/day through the pumps. The second group, which served as the control, received continuous infusion of 2.5M NaCl through the pumps. The third and fourth groups received a single intraperitoneal (IP) injection of MTX at 800 and 1000 $\mu$g/kg/injection respectively; the MTX injections were administered three times per week. Thus, the weekly dosage of MTX were 2.4 mg/kg/week and 3 mg/kg/week, respectively.

B. Result

Figure 8:
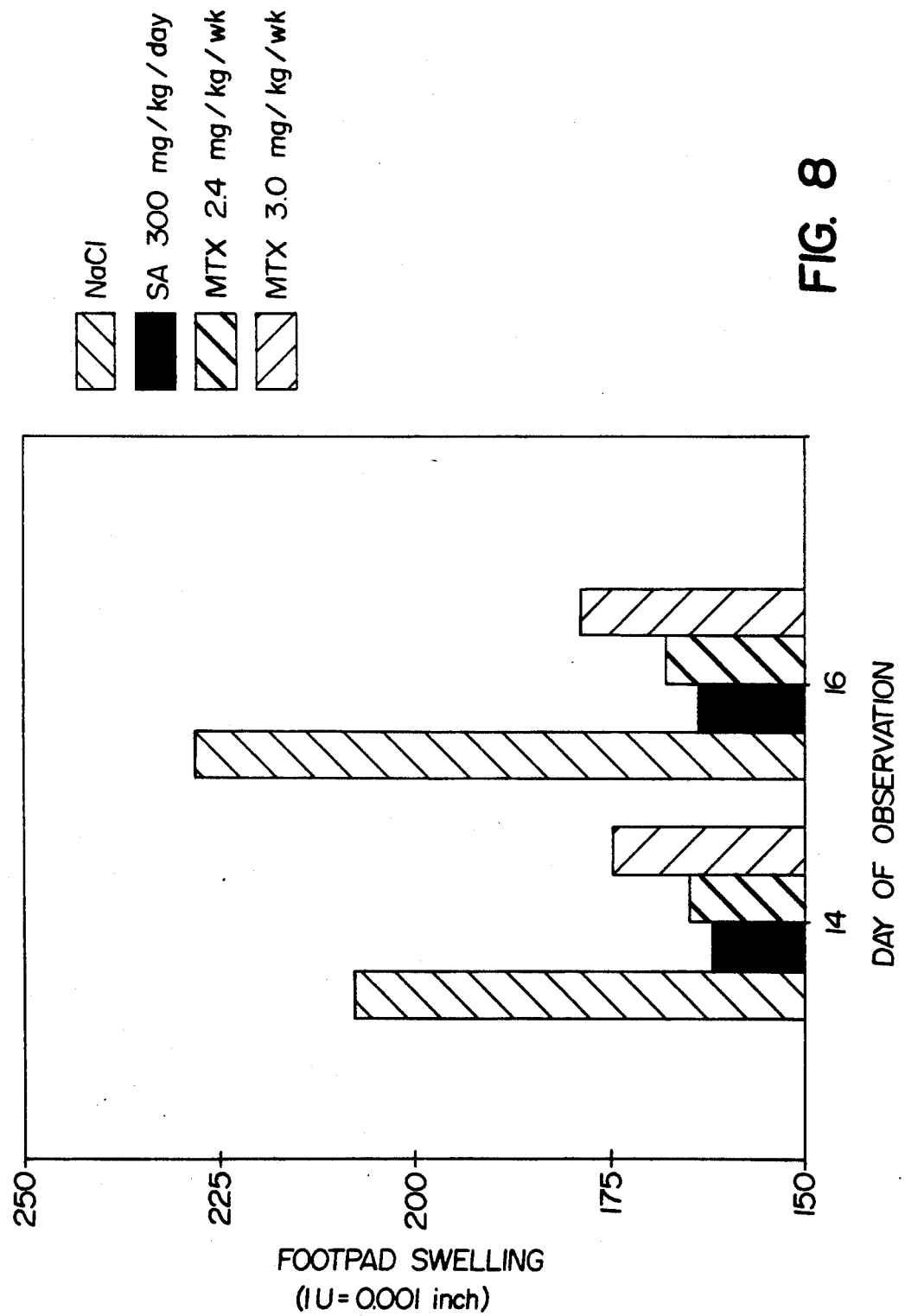
FIG. 8 presents the relative efficacy of SA and MTX in preventing the progression of established AA in rats.
Figure 9:
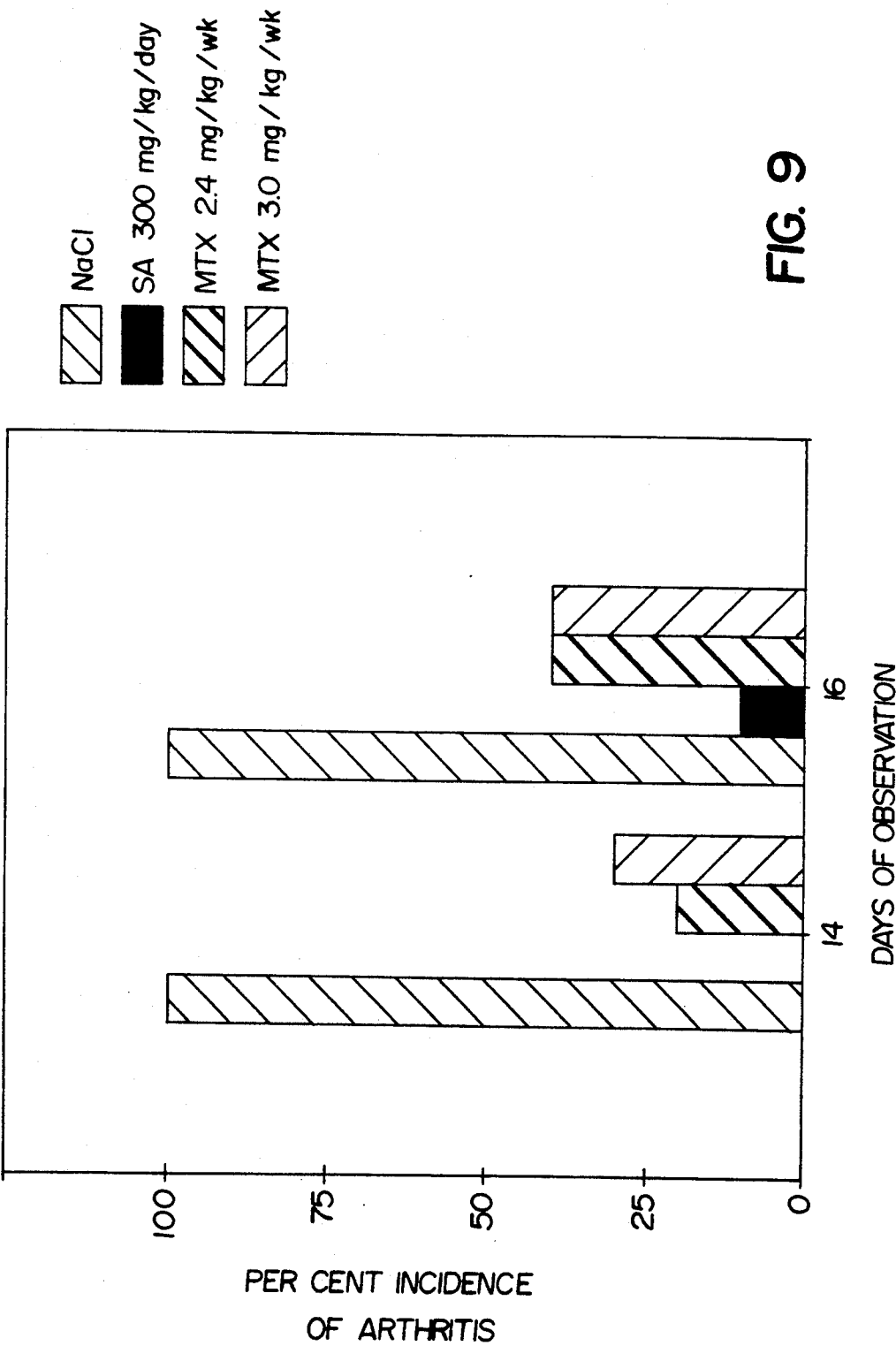
FIG. 9 compares the incidence of arthritis during treatment with SA versus MTX.

As in Example 1, the footpad swelling measurement and disease incidence of all the rats were noted (FIGS. 8 and 9, respectively). In FIG. 9, the group of rats treated with 300 mg/kg/day of SA showed no incidence of arthritis on day 14. The footpad swelling measurements showed significant suppression by both MTX and SA, with SA showing a trend towards greater inhibition. SA also provided maximal suppression of AA based on the disease incidence.

EXAMPLE 4

Comparative Efficacy of SA and MTX in the Treatment of Established Arthritis

In this example, the effects of SA and MTX on established arthritis was investigated. The rats received SA and MTX on day 16 post-immunization with M.Tb.

A. Material and Method

Three groups of 15 male Lewis rats were injected with M.Tb on day 0 in the left hindpaw. All rats had developed clinical arthritis by day 16. On day 16, subcutaneous pumps were placed in the SA and control groups. SA was administered at 300 mg/kg/day by CI. The control group received 2.5M NaCl. MTX was administered 1 IP injection, three times a week at a total of 2.4 mg/kg/week. Treatment was continued to day 30.

B. Result

Figure 10:
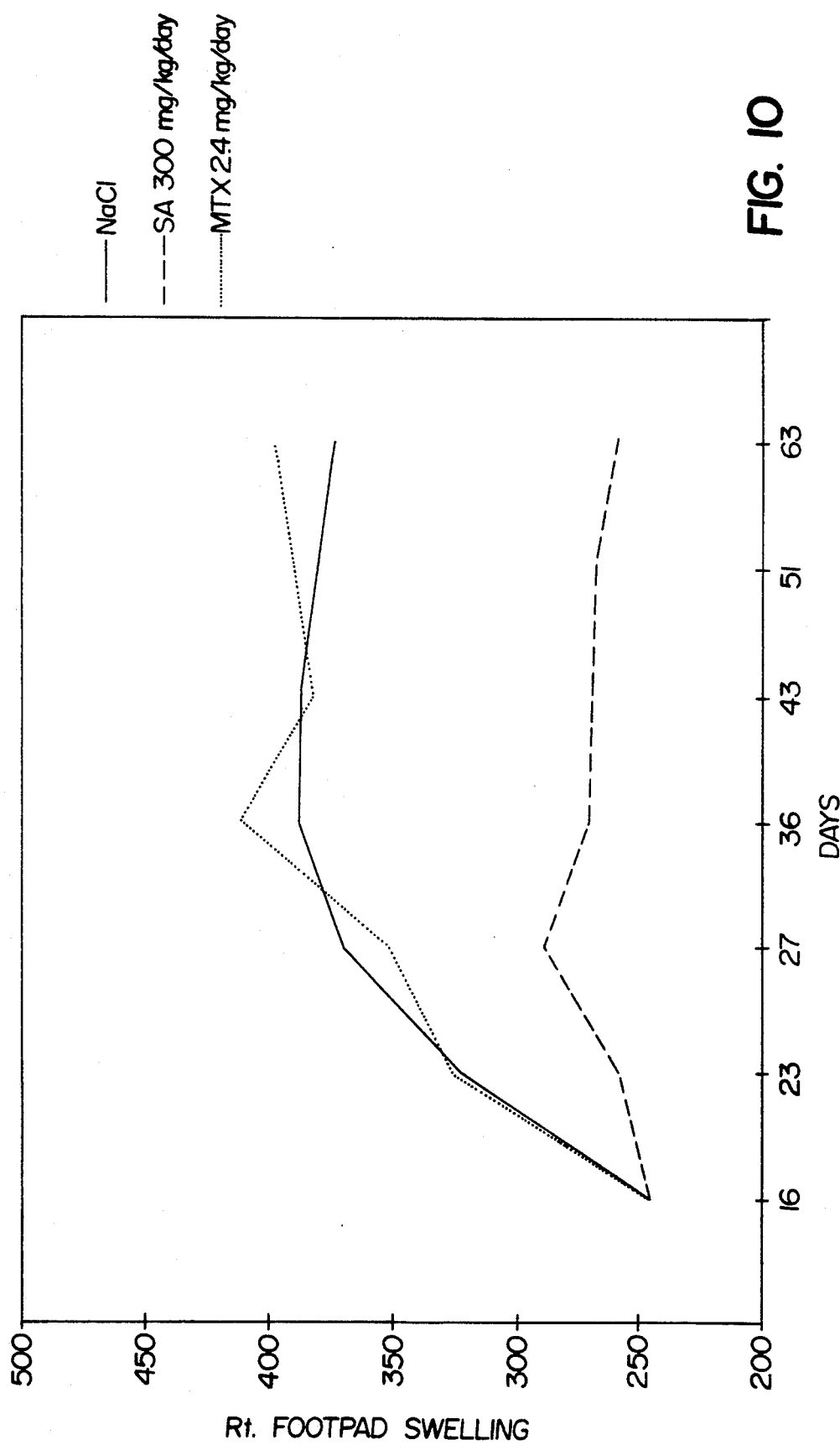
FIG. 10 shows that SA treatment prevents the progression of established arthritis in the rat AA model.

SA treated animals had an initial mean right hindpaw thickness of 258 U on day 23 (see FIG. 10). In contrast, the mean footpad thickness of the animals' right hindpaws in the control and MTX treated groups were 321 and 324, respectively. Normal animals have an average hindpaw footpad thickness of about 170 U at this age. From day 23 to 63 the right footpad diameters of the rats treated with SA did not increase significantly. In contrast, further progression of the right footpad swelling was seen in the control and MTX treated animals. The lack of further swelling in the SA treated animals persisted for up to 33 days after the cessation of treatment. Regression of disease was not seen and this was probably due to the rapid bone destruction that typically occurred in the rat AA model. Significant bone destruction had probably occurred before treatment was instituted. The experiment indicates that SA prevented progression of AA, but because the disease had already established itself at the onset of treatment, SA did not cause regression of the arthritis.

EXAMPLE 5

Combined SA and MTX Treatment

The following experiment shows that a treatment combining SA and MTX was more effective at treating AA than treatment using either drug alone at the same doses.

A. Method and Procedure

AA was induced in male Lewis rats as in the previous examples. On day 5, subcutaneous pumps were placed in all the rats. Seven groups of rats were used, the rats were treated in the following manner: 1) control, continuous infusion of 2.5M NaCl as previous Example, 2) continuous infusion of SA at 300 mg/kg/day, 3) continuous infusion of SA at 150 mg/kg/day, 4) 0.9 mg/kg/week of MTX, 5) 2.4 mg/kg/week of MTX, 6) 4.8 mg/kg/week of MTX, and 7) continuous infusion of SA at 150 mg/kg/day in combination with IP injection of MTX at 0.9 mg/kg/week. In all cases, the MTX was administered as a single IP injection three times a week in equal doses.

B. Result

Figure 11:
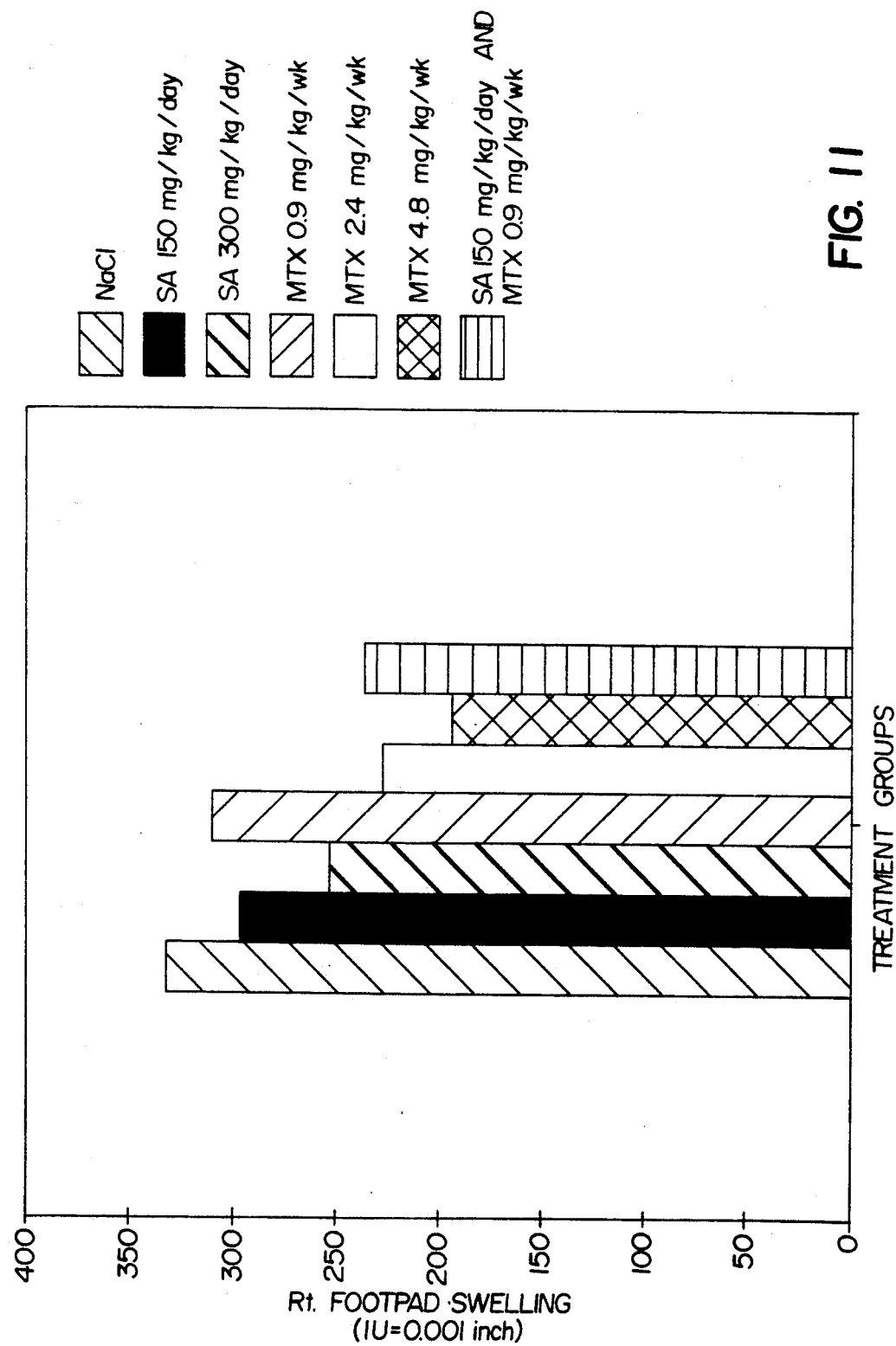
FIG. 11 presents the result of combined SA and MTX treatment in suppressing AA.

The results on the suppression of AA, as indicated by the right footpad swelling measurements, are shown in FIG. 11. They indicated that the combined SA and MTX was more effective than treatment with either drug alone at these doses. Maximal efficacy was seen with MTX at 4.8 mg/kg/week. However, at 4.8 mg/kg/week, the MTX showed toxicity in that some of the rats died or suffered from bleeding noses. The result suggested that where SA and MTX were used in AA treatment during the same period, a lower dose of both SA and MTX was required to achieve the result as when the SA or MTX was the only treatment used. Further, in the combined treatment, the lowered MTX dose reduced its toxic effect.

EXAMPLE 6

Long Term Suppression of AA Using Combined SA and MTX Treatment

The following experiment shows that the combined SA and MTX treatment continued to exert a long term suppression of AA, even after the treatment had stopped.

A. Method

On day 0, three groups of 10 male Lewis rats were injected with M.Tb in oil suspension, as in previous examples. From day 5 to 15, the rats were treated with intraperitoneal injections of SA and MTX. The three groups were treated respectively with: 1) 300 mg/kg/day of SA, IP, daily, 2) 0.9 mg/kg/week of MTX, IP, 3 times/week, in equal doses, and 3) a combination of 1) and 2) together. The animals were evaluated for arthritis development.

B. Results

Figure 12:
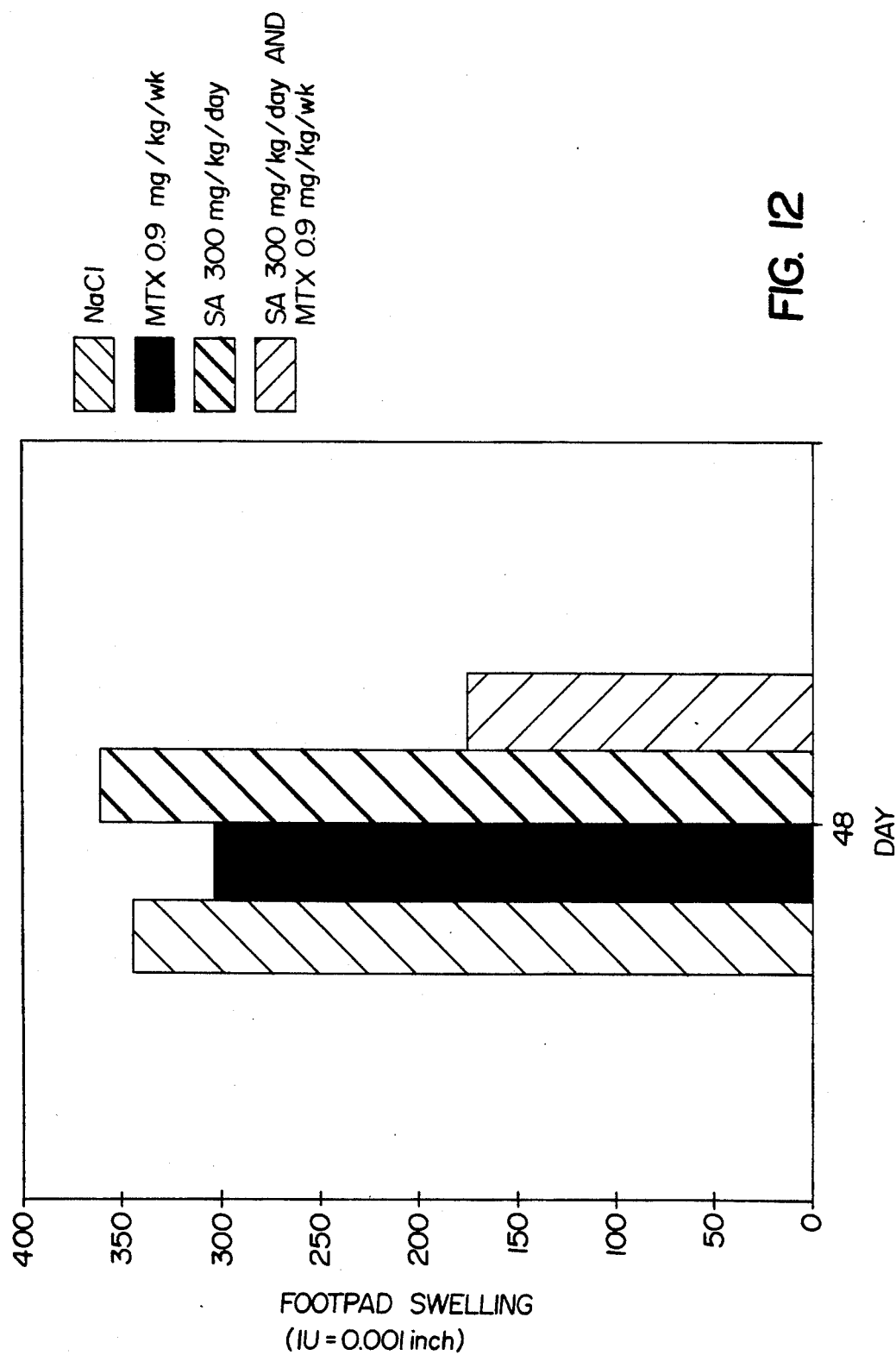
FIGS. 12 and 13 present the results of the long term efficacy of combined SA and MTX treatment.
Figure 13:
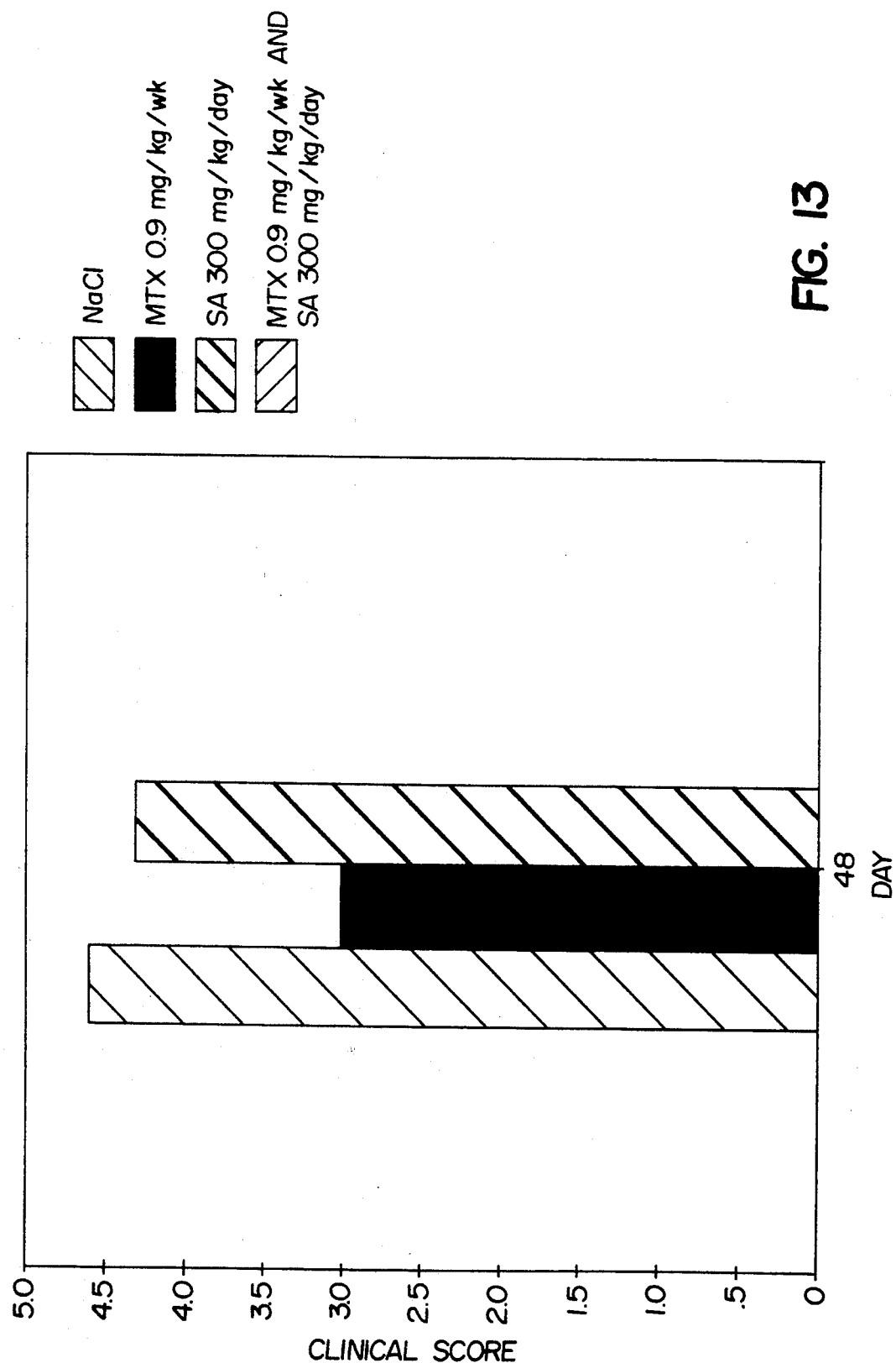

At the doses given, AA was not suppressed in the groups treated with either SA or MTX alone. The surprising result in this example was that a combined SA and MTX given intraperitoneally resulted in long term suppression of arthritis. The results are presented in FIGS. 12 and 13. In FIG. 13, the group of rats receiving the combined SA and MTX treatment showed no observable clinical signs of arthritis, i.e. their clinical scores were zero. FIG. 12 shows the average right footpad thickness of the rats in the combined SA and MTX treatment group was comparable to normal rats (170 U at their age). FIGS. 12 and 13 clearly shows that compared to the other treatment regimens, the combined SA and MTX treatment achieved the best result at day 48 post immunization, i.e. 33 days after termination of the combined SA and MTX treatment.

The above experiment presents a surprising result by indicating that the combined SA and MTX treatment has a suppressive effect long after the treatment had stopped, i.e., the effect was still felt 33 days after the treatment had been terminated. This has the advantage of eliminating the need of a continuous infusion of SA for the treatment of RA. Thus, for example, in the combined SA and MTX treatment, the animal afflicted with RA may orally take SA capsules on alternate days, and the MTX capsules on a weekly basis. Further, the previous treatment using IP injections of SA alone did not suppress the AA beyond the termination of the treatment regimen, even though the SA dosage used was comparatively higher at 800 mg/kg/day (FIG. 7). On the other hand, in the combined SA and MTX IP treatment, only 300 mg/kg/day of SA was required to show significant suppression (FIG. 13).

EXAMPLE 7

Class of ACA Compounds for the Treatment of Diseases Arising from Abnormal or Undesirable Normal Immune Responses In this example, the general synthesis method of ACA through Paths A and B are presented. The preferred examples of these synthesis are presented below.

According to Path A, an appropriately protected methyl ketone is converted to the enolate anion by the action of a strong base (such as alkali metal hydrides or alkoxides) and the anion acylated by an appropriate acetylating reagent (such as acetic anhydride, acetyl chloride, or esters of acetic acid). The reaction may be conducted in an inert solvent (such as tetrahydrofuran) or in the acetylating reagent itself (when the acetylating reagent is ethyl acetate or another ester of acetic acid). Following the completion of the acetylation reaction, the excess acylating reagent is removed and the product purified by extraction, chromatography, distillation or other methods.

According to Path B, a mono-ester of a dicarboxylic acid is converted to corresponding acyl chloride monoester by appropriate reagents (such as oxalyl chloride, thionyl chloride, phosphorus trichloride, etc.) in a compatible organic solvent (such as methylene chloride, tetrahydrofuran, ether, etc.). The acyl chloride is reacted with the anion of acetoacetate ester (such as the magnesium complex of t-butyl acetoacetate) to yield the intermediate acylated acetoacetate. This intermediate is converted to the desired product (a beta-diketone) via de-esterification of the acetoacetate followed by decarboxylation under appropriate conditions. The product may be purified by chromatography, crystallization, distillation or other methods.

The following are specific examples for generally obtaining the class of ACA compounds:

A. Example of Path A Synthesis of ACA

To a suspension of sodium hydride (oil free; 7.2 gm; 300 mM) in 100 ml of tetrahydrofuran (THF) containing acetone (7.4 ml; 5.81 gm; 100 mM) is added a solution of mono-methyl phthalate (18.0 gm; 100 mM) in 50 ml of THF (addition was made dropwise with stirring). After the addition is complete, the mixture is refluxed for one hour (no further gas evolved). To the cooled mixture is added 100 ml of water. The layers are separated and the alkaline aqueous layer is extracted with ethyl acetate (2×100 ml). The aqueous layer is carefully acidified to pH 2 with concentrated sulfuric acid and extracted with ethyl acetate (3×100 ml). Analysis by thin layer chromatography (silica gel; ethyl acetate:hexane:acetic acid 50:50:1) shows no starting material remaining in aqueous layer. The combined organic extracts are dried over sodium sulfate, filtered and taken to dryness, and azeotroped with toluene to remove the last traces of moisture. The residue is taken up in hot water and allowed to cool to yield crystals.

B. Example of Path B Synthesis of ACA

To a suspension of mono-methyl phthalic acid (28.54 gm; 158 mM) in 200 ml of methylene chloride containing 1 ml of dimethylformamide is added oxalyl chloride (15.11 ml; 173 mM) dropwise with stirring at room temperature. Gas evolved and all material goes into solution. After one hour at room temperature, the solvent is removed under reduced pressure and the residue suspended in 100 ml ether. This suspension is added to a stirred suspension of the magnesium methoxide complex of t-butyl acetoacetate (30.6 gm; 144 mM) in 100 ml ether. The mixture is stirred at room temperature overnight. The next morning 150 ml of 1.8M sulfuric acid is added and the two-phase mixture transferred to a 1 L separatory funnel. The ether layer is removed and the aqueous layer extracted with ether (2×100 ml). The pooled ether extracts are dried over sodium sulfate, filtered and taken to an oily residue. This is fractionated on a silica gel column using ethyl acetate:hexane at the ratio of 1:4 as eluant. Fractions containing the intermediate product, 2-(2-t-butyloxycarbony) acetoacetyl benzoic acid, are pooled and concentrated to an oil (37.2 gm; 116 mM; 81%). The oil is suspended in 600 ml of 4N hydrochloric acid and heated to reflux for two hours. Thin layer chromatography (silica gel; ethyl acetate:hexane:acetic acid 50:50:1) shows no starting material remaining. The solvent is removed under reduced pressure at 50° C., and the residue purified by silica gel column chromatography using the TLC solvent. The fractions containing product are pooled and concentrated to a residue which is crystallized from hot water to yield 5.7 gms (28 mM; 18%).

The compounds arrived at by Paths A or B above could be further dimethylated, into compounds having a (2,2-dimethyl) group. The general method for dimethylation is presented in Choudary, A., et al., *Synthesis*, 1989, 9: 688, entitled "Convenient, High-Yield Method for the Methylation of 1,3-Diketones". Further, with slight modification, the same process may be used for monomethylation of the compounds. Id.

The following are examples of compounds in the ACA class:

2-acetoacetyl benzoic acid (ABA)

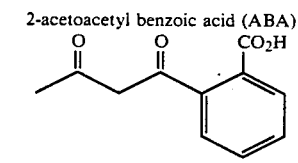

I.

3-acetoacetyl benzoic acid

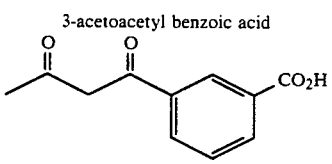

II.

4-acetoacetyl benzoic acid

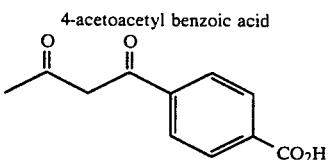

III.

3-acetoacetyl 4-carboxy pyridine

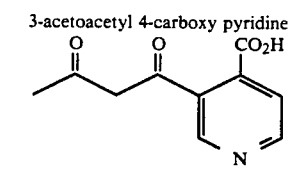

IV.

4-acetoacetyl 3-carboxy benzene sulfonic acid

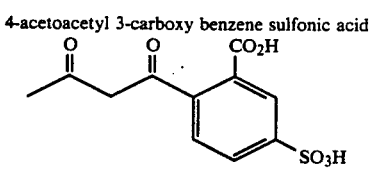

V.

4-acetoacetyl 3-carboxy furan

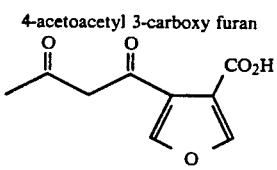

VI.

5-acetoacetyl 4-carboxy imidazole

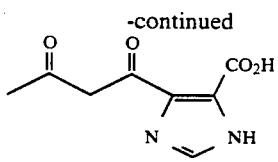

VII.

2-acetoacetyl cyclohexane carboxylic acid (cis or trans)

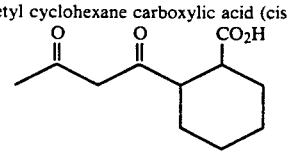

VIII.

3-acetoacetyl cyclohexane carboxylic acid (cis or trans)

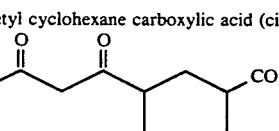

IX.

4-acetoacetyl cyclohexane carboxylic acid (cis or trans)

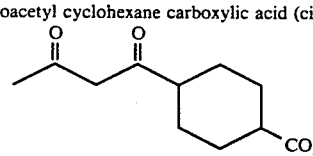

X.

2-acetoacetyl cyclopentane carboxylic acid (cis or trans) (and 3-acetoacetyl isomer)

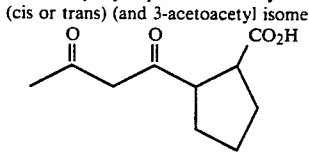

XI.

2-acetoacetyl cyclopropane carboxylic acid (also 2-acetoacetyl cyclobutane carboxylic acid) (cis or trans) (and 3-acetoacetyl isomer)

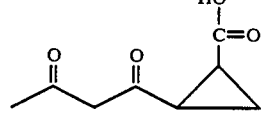

XII.

An example of a dimethylated derivative of ACA is the dimethylated modification of ABA, with the chemical name and formula of: 2-(2,2-dimethyl) acetoacetyl benzoic acid

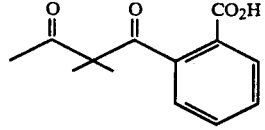

The above synthesis methods can be modified by one skilled in the art to achieve the individual compounds presented above. The preferred ACA is 2-acetoacetyl benzoic acid (ABA). The following presents the synthesis of ABA, its immunosuppressive characterization, and its use in the treatment of AA.

C. Synthesis of 2-Acetoacetyl Benzoic Acid (ABA)

This synthesis follows the general procedure of Path B synthesis above with minor modifications to produce the specific ABA. To a suspension of mono-methyl phthalic acid (1.98 gm: 11 mmole) in 20 ml of dichloromethane containing 100 μl of DMF was added oxalyl chloride (1.06 ml; 1.54 gm; 12 mmole). Gas evolved and all material dissolved. After one hour at room temperature the solvent was removed under reduced pressure and the residue suspended in 10 ml ether. This suspension was added to a suspension of the magnesium complex of t-butyl acetoacetate (J. Chem. Soc. Perkin Trans. I (1981) pg. 2792) (2.13 gm: 10 mmole) in 10 ml ether. This mixture was refluxed for 30 minutes and allowed to cool. To the cooled mixture was added 10 ml of 1.8N aqueous sulfuric acid. The combined ether extracts were aqueous phase extracted with ether (3×10 ml). The combined ether extracts were dried over sodium sulfate, filtered and taken to dryness azeotroped with toluene and the residue fractionated by silica gel column flash chromatography using ethyl acetate:hexane 1:4 as eluant. Fractions containing product were pooled and concentrated to yield 2.16 gm (6.74 mmole; 67%) of the intermediate product, Compound I. Rf=0.45 (silica gel, ethyl acetate:hexane 1:4 UV positive, red brown spot when sprayed with 2.7% w/v ferric chloride in 2N aq. HCl).

Compound I (2.0 gm; 6.24 mmole) was refluxed in 40 ml of 4N aqueous HCl for two hours. A solution resulted and the solution was allowed to cool. The solvent was removed under reduced pressure and the residue fractionated by silica gel column flash chromatography using ethyl acetate:hexane:acetic acid 50:50:1 as eluant. Fractions containing the product were pooled and taken to dryness. The residue was taken up in hot water, treated with decolorizing carbon, filtered and chilled overnight. Crystals formed and were collected by filtration and dried under vacuum to yield 470 mg (37%). The crystals had an Rf of 0.35 (silica gel, ethyl acetate:hexane:acetic acid 50:50:1), were UV positive; and formed purple spot with ferric chloride/HCl spray reagent.

D. Immunosuppressive Activities of ABA

1. Primary Mixed Lymphocyte and Phytohemagglutinin Assays

The following studies sought to characterize the immunosuppressive activities of ABA, both as to in vitro and in vivo efficacy in experimental systems. It is important to point out that the results obtained from the in vitro systems are generally predictive of the in vivo immunosuppressive properties of the ABA. More specifically, the assays used here are mixed lymphocyte response (MLR) and phytohemagglutinin A (PHA) assays which are valuable for identifying immune suppressive molecules in vitro, and that the results obtained therefrom are generally predictive of their in vivo effectiveness. The assays are further described below.

The in vitro mixed lymphocyte assay is presently employed in the clinical setting as an indicator of histocompatibility, and is premised on the transformation of resting genetically dissimilar lymphocytes into cells which synthesize DNA and undergo proliferation. It has been demonstrated that incompatibility at the major histocompatibility complex is mainly responsible for this phenomenon.

A second assay widely used to study immune responsiveness is mitogenic stimulation of lymphocytes with mitogenic substances of plant origin. The most widely used plant molecule is PHA. Although PHA stimulates DNA synthesis non-specifically in a large number of lymphocytes, unlike true antigenic stimulation which causes mitogenesis of sub-populations of lymphocytes, the susceptibility of a patient's lymphocytes to PHA stimulation has been shown to correlate with the overall immune responsiveness of the patient.

Thus, it will be appreciated as to both the mixed lymphocyte and PHA assay that they are valuable for identifying immune suppressive molecules in vitro, and that the results obtained therefrom are generally predictive of their in vivo effectiveness.

2. Secondary Mixed Lymphocyte Assays

In addition to the above immunosuppressive assays, a secondary mixed lymphocyte reaction assay was applied to ABA. The secondary mixed lymphocyte assays differs from the primary mixed lymphocyte reaction assays in that they employ many more primed responder cells that are responsive to the primary stimulating cells. The presence of such responsive cells is a reflection of immunological memory in an ongoing immunological response. The protocol for carrying out a secondary mixed lymphocyte assay involves performing a primary lymphocyte assay as described above, and recovering viable cells about 9-10 days after the primary mixed lymphocyte reaction exhibits little or no cell proliferation. Generally between 10% to 50% of the original input cells are recovered in viable condition. These cells are then used in the secondary mixed lymphocyte reaction.

The procedure for carrying out a secondary mixed lymphocyte reaction is described by T. Meoen, *Immunological Methods*, Eds I. Lefkoivits and B. Pernis, Economic Press, New York (1979). It will be appreciated that described therein is a method for carrying out secondary lymphocyte reactions using mouse cells, however such methods are generally applicable to performing secondary mixed lymphocyte reactions using human cells with modifications that are well known to those skilled in the art.

3. Results of the Immunosuppressive Tests

Surprisingly, in the PHA and primary MLR assays, ABA gave 50% inhibitions at very low concentrations. The concentrations were $0.091 \pm 0.06$ mM, and $0.87 \pm 0.28$ mM. In the 2'-MLR, ABA inhibited 50% of the stimulatory activity at a concentration of about 1.6 mM.

E. Formulation for ABA

The following experiments sought to determine a functioning and yet relatively non-toxic formulation for ABA. The following formulations of ABA were tested.

1. Solubility of the Different Formulations In Vitro

The following were found to be non-soluble in vitro. Precipitation and aggregation in the test tube was found in the following formulations: ABA in 10% ethanol and 40% propylene glycol (PEG); and ABA in 50% PEG. Further, aggregation and clumps were found in the following formulations: ABA in 20% ethanol and 20% glycerin; ABA in 20% PEG and 5% ethanol.

2. In Vivo Treatments of AA Using Different Formulations of ABA

The following experiments tested three different formulations of ABA in vivo.

a) ABA in PEG

Materials & Procedure

It was found that there was no death in the rats treated with daily IP injection of 400 mg/kg/ml of ABA in a freshly prepared formulation comprising ABA, polypropylene glycol (PEG), and sodium hydroxide (the formulation is hereinafter referred to as "ABA/PEG formulation"). It should be noted that this formulation is preferably prepared prior to administration since it forms aggregates and precipitates and turns a yellow color on standing. A freshly prepared formulation does not precipitate, aggregate, nor clump in solution. The composition of the formulation is as follows:
975 mg of 2-acetoacetyl benzoic acid;
5.36 ml of 50% PEG;
487.5 µl of 10N NaOH (final pH=7.0); and
final concentration of 2-acetoacetyl benzoic acid is about 144 mg/ml.

The ABA/PEG formulation was formulated daily before injection. Male Lewis rats were injected with M.Tb/mineral oil on day 0. Daily IP injection of the ABA at doses of 400, 200 and 100 mg/kg/day were administered. The control rats received the same formulation as the ABA/PEG formulation, except that the ABA was replaced with an equivalent molarity of NaCl (hereinafter referred to as the NaCl/PEG formulation). There were 5 rats per group. Injections were performed from day 5 to 15.

Results

In previous studies it had been shown that SA was effective at a dose of 800 mg/kg/day IP when treatment began at day 5. (See Example 2). Here, in order to determine if ABA was more efficacious than SA, the maximum dose of ABA was 400 mg/kg/day Table 3 shows the results.

TABLE 3

| Treatment mg/kg/ml of ABA in ABA/PEG Formulation | Day | Arthritis Incidence % |
|---|---|---|
| 400 | 12 | 40 |
| 200 | 12 | 100 |
| 100 | 12 | 100 |
| Control: NaCl/PEG Formulation | 12 | 100 |
| 400 | 19 | 100 |
| 200 | 19 | 100 |
| 100 | 19 | 100 |
| Control: NaCl/PEG Formulation | 19 | 100 |

Figure 14:
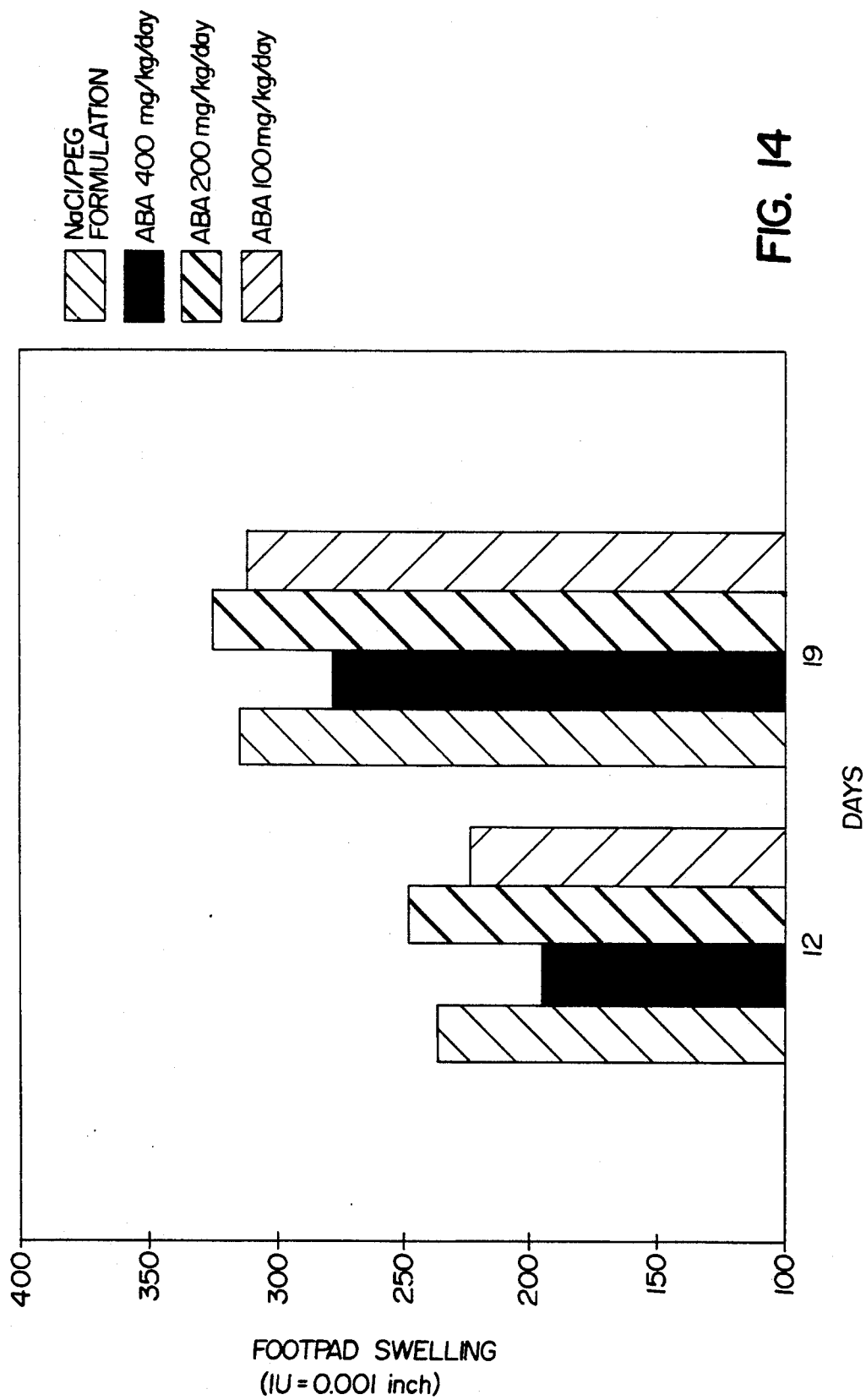
FIG. 14 presents the suppression by 2-acetoacetyl benzoic acid of footpad swelling in rats afflicted with AA.
Figure 15:
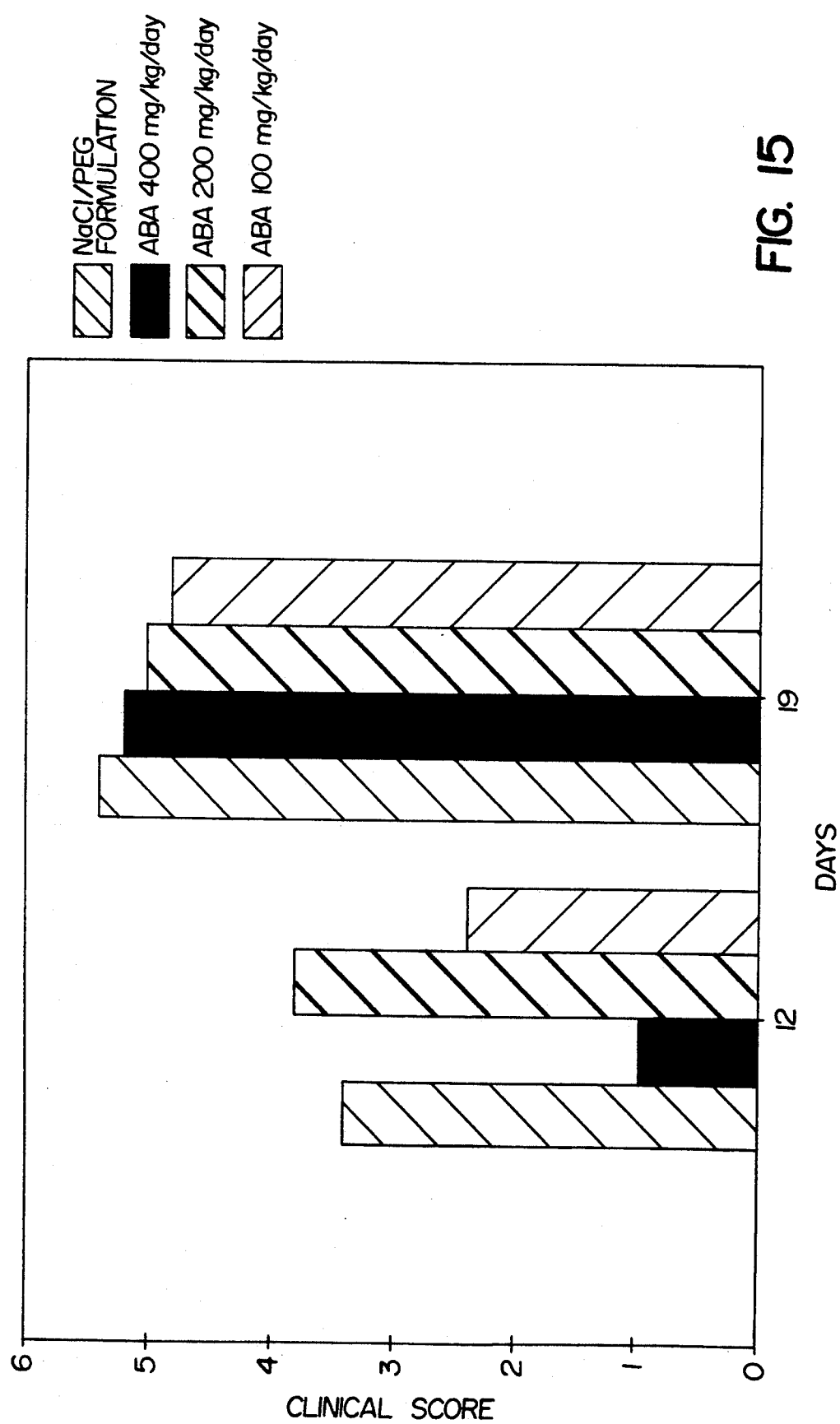
FIG. 15 presents the effects of 2-acetoacetyl benzoic acid on the clinical scores of rats afflicted with AA.

Table 3 shows that only 40% of the rats (i.e. 2 of the 5 rats) in the group receiving 400 mg/kg/day of ABA showed signs of arthritis. In contrast, the rats in the other treatment regimens and control all exhibited signs of arthritis. The effects of ABA in the ABA/PEG formulation on right footpad swelling and clinical scores were represented in FIGS. 14 and 15.

The result showed that during the administration of 400 mg/kg/day of ABA in the ABA/PEG formulation, AA was suppressed; the footpad swelling, clinical disease scores and incidence of arthritis were all lowered. By day 19, 4 days after cessation of treatment, the groups had comparable measurements, except for a decreased footpad swelling in the group receiving 400 mg/kg/day of ABA. When SA was given using this treatment protocol, it resulted in only transient suppression of the disease at a dose of 800 mg/kg/day. Since at a lower dose of 400 mg/kg/day, ABA achieved suppression of AA which suppression further persited after termination of the ABA treatment, ABA is more efficacious than SA in suppressing AA. 200 and 100 mg/kg/day of ABA did not show observable suppression of arthritis. In summary, ABA suppressed AA at 400 mg/kg/day when given IP in a post-immunization regimen.

EXAMPLE 8

Methods of Treatment of Rheumatoid Arthritis (RA)

The following example shows how the above compounds and their compositions can be used in treating diseases arising from abnormal or undesirable normal immune responses. Preferably, the diseases are autoimmune diseases. More preferably, the autoimmune disease is RA. The compounds and their compositions can be used to eradicate or reduce the severity of RA. Briefly, the afflicted animal is administered with an effective amount of ACA, or a combination of two or more of the following: SA, FA, and ACA. The preferred member of FA and ACA is MTX and ABA respectively. The above compounds can be administered individually or combined into compositions. These compounds and combinations are hereinafter referred to as "Compounds". The preferred animal subject is human. The animal can further be treated with disease modifying antirheumatic drugs (DMARDs), cytotoxic drugs, immunosuppressive drugs, and/or steroids.

The strategy used in treating a particular animal patient depends on its species, age, general health, status of RA, etc. For example, the desired dose of Compounds may be presented as two, three, four or more subdoses administered as infusions or taken orally at appropriate intervals throughout the treatment period. If administered as infusion, administration is by any suitable route such as parenteral (including subcutaneous, intramuscular, intravenous and intradermal). The preferred route is orally in the form of including, but not limited to, tablets or capsules. For example, the patient can take effective doses of MTX and SA tablets or capsules three times a week. It will be appreciated that the preferred route may vary based on the factors discussed above.

Currently, combination chemotherapy using two or more anti-arthritic drugs is used in research and clinics. Therefore, the administered Compounds may be used in therapy in conjunction with other medicaments such as cytotoxic drugs; immunosuppressive drugs, e.g. cyclosporin; steroids; and DMARDs which can include: gold, metal chelators such as D-penicillamine, anti-malarials such as chloroquine, dapsone, sulfasalazine and other traditional or new drugs used in the treatment of RA. Where one of the medicaments has side effects, it can be given to patients on alternate treatment periods. For example, MTX has toxic side effects, and can cause liver and kidney diseases. D-penicillamine is also toxic since it causes bone marrow depression and renal toxicity. Since MTX and D-penicillamine exhibit different toxicities, they are given to patients on alternate treatment periods. Additionally, in combination, the different drugs and the Compounds may exert synergistic effect. Further, the toxicities of the drugs may also be separate and not additive. There can be a trade-off between the toxicity and effectiveness of the drugs. In view of the above experiments, less of a toxic anti-arthritic drug may be used in the presence of SA, and yet the combination may achieve suppression of the disease, equivalent with higher dosage of the toxic anti-arthritis drug administered alone.

While the Compounds may be administered alone, they may be presented as part of a pharmaceutical formulation. Preferably, the Compounds are combined with an acceptable carrier. The formulations of this invention may include other agents conventional in the art having regard to the type of formulation in question. The formulations can also include other anti-arthritis drugs such as cytotoxic drugs; immunosuppressive drugs; steroids; and DMARDs. The carrier must be "acceptable" in the sense of being compatible with the other ingredients of the formulation and not deleterious to the recipient.

The following is an example of the procedure for administering a combined SA and MTX treatment to a human patient. The patient takes a tablet or capsule of SA daily at a total weekly dose of 50 to 300 mg/kg/day. During the same period, the patient also takes a tablet or capsule of MTX three times a week, at a total weekly dose of 10 to 50 mg/patient/week. Preferably, the patient is treated with a starting dose of MTX at 10 mg/week. The dosage is increased by 5 mg every 2 to 3 weeks. The maximum level of dosage is determined at the point at which the patient shows improvements. At the end of the five-day period, the patient is evaluated. The evaluation includes physical examination and extensive laboratory testing. The tests include evaluation for toxicity. The additional laboratory monitoring in the case of MTX preferably includes complete blood cell count every 2 weeks for the first 3 months and then monthly thereafter. Additional precautions preferably include monthly assessments of levels of serum albumin, alanine amino transferase, bilirubin, creatinine, and blood urea nitrogen. Monthly urinalysis is also preferred.

The dosage would be varied taking into consideration the individual patient's tolerance of the drug, its efficacy and toxicity. Other anti-arthritis drugs mentioned above can be used in combination with the treatments. According to results of the above tests, the starting dose of the particular Compound(s) used is/are reduced for a patient who exhibits adverse reaction, or the drug used in combination with the Compound(s) can be changed or reduced.

The tests for monitoring the improvement of the disease can include specific tests directed, for example, to the determination of systemic response to inflammation, which includes erythrocyte sedimentation rate (ESR), and acute phase reactants (APR). Observations were made of the swelling, etc., of the afflicted body parts. Improvement in stiffness, grip (where applicable) and pain of the patient is also observed. If the patient's condition is stable, he is re-treated at the same dosage weekly and evaluated weekly. Provided the patient's condition is stable, the treatment may be continued. After six months of treatment, anatomical changes of skeleton is determined by radiologic imaging, for example by X-radiography.

At the end of each period, the patient is again evaluated. Comparison of the pre-treatment and post-treatment radiological assessment, erythrocyte sedimentation rate (ESR), and acute phase reactants (APR) indicate the efficacy of the treatments. According to the efficacy of the treatments, and the patient's condition, the dosage of SA and MTX may be increased or maintained constant for the duration of treatment.

Similarly, the above regimen can utilize ACA alone or in combination with a FA and/or SA. The ACA can be in the form of a pharmaceutically acceptable excipients. The pharmaceutical carrier may also serve to reduce the toxicity of the Compounds used. For example, the preferred ACA is ABA in the PEG formulation.

The above is by way of example, and does not preclude the treatment of other diseases arising from abnormal or undesirable normal immune responses. Further, the methods of treatment e.g., doses and methods of administering the Compound(s) may be varied to achieve a desired result. The Compound(s) also include compositions, or compounds comprising ACA, or a combination of two or more of the following: SA, FA, and ACA alone or in combination with other antiarthritis drugs mentioned above. The example also does not preclude other treatments to be used concurrent with these Compounds that are known by those skilled in the art, or that could be arrived at by those skilled in the art using the guidelines set forth in this specification.

In summary, the present invention has been described with reference to specific embodiments. However, this application is intended to cover those changes and substitutions which may be made by those skilled in the art without departing from the spirit and the scope of the appended claims.

We claim:

1. A method for preventing or treating rheumatoid arthritis in an animal, comprising administering to the animal therapeutically effective amounts of SA and MTX, wherein said SA and MTX are administered separately or in combination.

2. A composition for preventing or treating rheumatoid arthritis in an animal, wherein the composition comprises SA and MTX.

* * * * *